US009460264B2

(12) United States Patent
Bangera et al.

(10) Patent No.: US 9,460,264 B2
(45) Date of Patent: *Oct. 4, 2016

(54) DEVICES, SYSTEMS, AND METHODS FOR AUTOMATED DATA COLLECTION

(75) Inventors: Mahalaxmi Gita Bangera, Renton, WA (US); Michael H. Baym, Cambridge, MA (US); Philip A. Eckhoff, Bellevue, WA (US); Roderick A. Hyde, Redmond, WA (US); Muriel Y. Ishikawa, Livermore, CA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 759 days.

This patent is subject to a terminal disclaimer.

(21) Appl. No.: 13/463,997

(22) Filed: May 4, 2012

(65) Prior Publication Data

US 2013/0297219 A1 Nov. 7, 2013

Related U.S. Application Data

(63) Continuation-in-part of application No. 13/463,945, filed on May 4, 2012, and a continuation-in-part of application No. 13/463,975, filed on May 4, 2012, now Pat. No. 9,317,662.

(51) Int. Cl.
G01N 33/48 (2006.01)
G06F 19/00 (2011.01)

(52) U.S. Cl.
CPC ......... *G06F 19/345* (2013.01); *G06F 19/3431* (2013.01); *G06F 19/322* (2013.01); *G06F 19/327* (2013.01)

(58) Field of Classification Search
CPC .................................................. G06F 19/345
USPC .......................................................... 702/19
See application file for complete search history.

(56) References Cited

U.S. PATENT DOCUMENTS

| | | |
|---|---|---|
| 4,703,756 A | 11/1987 | Gough et al. |
| 5,338,625 A | 8/1994 | Bates et al. |
| 5,372,136 A | 12/1994 | Steuer et al. |
| 5,571,152 A | 11/1996 | Chen et al. |
| 5,582,170 A | 12/1996 | Soller |
| 5,603,820 A | 2/1997 | Malinski et al. |
| 6,097,295 A | 8/2000 | Griesinger et al. |
| 6,167,298 A | 12/2000 | Levin |
| 6,210,326 B1 | 4/2001 | Ehwald |
| 6,234,973 B1 | 5/2001 | Meador et al. |
| 6,268,161 B1 | 7/2001 | Han et al. |
| 6,280,604 B1 | 8/2001 | Allen et al. |
| 6,287,452 B1 | 9/2001 | Allen et al. |
| 6,442,413 B1 | 8/2002 | Silver |
| 6,475,161 B2 | 11/2002 | Teicher et al. |
| 6,514,689 B2 | 2/2003 | Han et al. |
| 6,546,268 B1 | 4/2003 | Ishikawa et al. |
| 6,650,746 B1 | 11/2003 | Groen et al. |
| 6,764,446 B2 | 7/2004 | Wolinsky et al. |
| 6,786,406 B1 | 9/2004 | Maningas |
| 6,818,356 B1 | 11/2004 | Bates |
| 6,823,717 B2 | 11/2004 | Porter et al. |
| 6,965,791 B1 | 11/2005 | Hitchcock et al. |
| 6,994,934 B2 | 2/2006 | Stanish et al. |
| 7,135,987 B1 | 11/2006 | LaMotte et al. |
| 7,144,655 B2 | 12/2006 | Jenson et al. |
| 7,162,289 B2 | 1/2007 | Shah et al. |
| 7,168,294 B2 | 1/2007 | Porter et al. |
| 7,189,471 B2 | 3/2007 | Jankowksi et al. |
| 7,194,801 B2 | 3/2007 | Jenson et al. |
| 7,205,701 B2 | 4/2007 | Liu et al. |
| 7,206,605 B2 | 4/2007 | Hattori |
| 7,215,887 B2 | 5/2007 | Ternullo et al. |
| 7,218,900 B2 | 5/2007 | Suzuki |
| 7,226,164 B2 | 6/2007 | Abourizk et al. |
| 7,227,956 B1 | 6/2007 | Onishi |
| 7,236,595 B1 | 6/2007 | Bean et al. |
| 7,238,628 B2 | 7/2007 | Demaray et al. |
| 7,245,894 B2 | 7/2007 | Sekiguchi et al. |
| 7,245,956 B2 | 7/2007 | Matthews et al. |
| RE39,785 E | 8/2007 | Fuse |
| 7,254,160 B2 | 8/2007 | Kawamoto et al. |

(Continued)

FOREIGN PATENT DOCUMENTS

| | | |
|---|---|---|
| WO | WO 03/048789 A2 | 6/2003 |
| WO | WO 2006/091123 A1 | 8/2006 |

(Continued)

OTHER PUBLICATIONS

PCT International Search Report; International App. No. PCT/US2013/039380; Aug. 16, 2013; pp. 1-2.
American Academy of Sleep Medicine, International Classification of Sleep Disorders: Diagnostic and Coding Manual; $2^{nd}$ ed. 2005; two pages of book description printed on Apr. 2, 2012.
Avagyan et al.; "New Diagnostic Methods in Acupuncture"; ICMART '99 International Medical Acupuncture Symposium, Riga, May 21-23, 1999; p. 7.
Banerjee et al.; "Telesurveillance of elderly patients by use of passive infra-red sensors in a 'smart' room"; Journal of Telemedicine and Telecare; Feb. 1, 2003; pp. 23-29; vol. 9, No. 1; Royal Society of Medicine Press Limited.
Black et al.; "Narcolepsy and Syndromes of Central Nervous System-Mediated Sleepiness"; Focus; Fall 2005; pp. 585-597; vol. III, No. 4.
Black et al.; "Narcolepsy and Syndromes of Primary Excessive Daytime Somnolence"; Seminars in Neurology; 2004; pp. 271-282; vol. 24, No. 3; Thieme Medical Publishers, Inc.

(Continued)

*Primary Examiner* — Jerry Lin

(57) ABSTRACT

Embodiments disclosed herein relate to methods, devices, and computer systems thereof for automated data collection from a subject. In certain embodiments, one or more characteristics of a subject are sensed, and the subject is given a queue status indicator based on a comparison of the subject's one or more sensed characteristics with corresponding sensed characteristics from other subjects. In one embodiment, the subject is a healthcare worker and the system, methods, and devices are utilized to evaluate the overall health of the worker as part of the check-in process for work.

20 Claims, 7 Drawing Sheets

(56) References Cited

U.S. PATENT DOCUMENTS

| | | |
|---|---|---|
| 7,254,439 B2 | 8/2007 | Misczynski et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B1 | 8/2007 | Matsumoto et al. |
| 7,272,431 B2 | 9/2007 | McGrath |
| 7,291,503 B2 | 11/2007 | Swager |
| 7,340,293 B2 | 3/2008 | McQuilkin |
| 2001/0039503 A1 | 11/2001 | Chan et al. |
| 2002/0173928 A1 | 11/2002 | Willner et al. |
| 2003/0212575 A1 | 11/2003 | Saalsaa et al. |
| 2004/0006257 A1 | 1/2004 | Burch et al. |
| 2004/0123667 A1 | 7/2004 | McGrath |
| 2004/0138924 A1 | 7/2004 | Pristine |
| 2004/0147818 A1 | 7/2004 | Levy et al. |
| 2005/0144038 A1 | 6/2005 | Tamblyn et al. |
| 2006/0058694 A1 | 3/2006 | Clark et al. |
| 2006/0190419 A1 | 8/2006 | Bunn et al. |
| 2006/0212085 A1 | 9/2006 | Fischell et al. |
| 2006/0229919 A1 | 10/2006 | Pugh |
| 2006/0253300 A1 | 11/2006 | Somberg et al. |
| 2006/0280307 A1 | 12/2006 | Ikushima et al. |
| 2007/0088713 A1 | 4/2007 | Baxter et al. |
| 2007/0125844 A1 | 6/2007 | Libin et al. |
| 2007/0138253 A1 | 6/2007 | Libin et al. |
| 2008/0039698 A1 | 2/2008 | Burton |
| 2008/0045832 A1 | 2/2008 | McGrath |
| 2008/0243542 A1 | 10/2008 | Hammond et al. |
| 2008/0246495 A1 | 10/2008 | Zarabadi et al. |
| 2009/0036780 A1 | 2/2009 | Abraham |
| 2010/0019910 A1 | 1/2010 | Hassing et al. |
| 2010/0049095 A1 | 2/2010 | Bunn et al. |
| 2010/0080431 A1 | 4/2010 | Datema et al. |
| 2010/0125182 A1 | 5/2010 | Schroeter et al. |
| 2010/0140110 A1 | 6/2010 | Kim et al. |
| 2010/0174533 A1 | 7/2010 | Pakhomov |
| 2011/0313783 A1 | 12/2011 | Sacco et al. |

FOREIGN PATENT DOCUMENTS

| | | |
|---|---|---|
| WO | WO 2008/019800 A1 | 2/2008 |
| WO | WO 2010/104978 A2 | 9/2010 |

OTHER PUBLICATIONS

Biometric Iris Access Control Scanner: Iris Access 4000—Biometric Authentication; product specifications; printed on Oct. 20, 2011 and PDF created on Feb. 16, 2013; 3 pages; located at www.bavometric.com.

Buckley et al.; "Review: On the Interactions of the Hypothalamic-Pituitary-Adrenal (HPA) Axis and Sleep: Normal HPA Axis Activity and Circadian Rhythm, Exemplary Sleep Disorders"; The Journal of Clinical Endocrinology & Metabolism; 2005; pp. 3106-3114; vol. 90, No. 5; The Endocrine Society.

Burke et al.; "Artificial intelligence in emergency department triage"; J Ambulatory Care Manage; Jul. 1990; pp. 50-54; vol. 13, No. 3.

Chen et al.; "A Microfluidic System for Saliva-Based Detection of Infectious Diseases"; Ann. N.Y. Acad. Sci; 2007; pp. 429-436; vol. 1098; New York Academy of Sciences.

Cook et al.; "Ambient Intelligence and Wearable Computing: Sensors on the Body, in the Home, and Beyond"; J Ambient Intell Smart Environ.; Jan. 1, 2009; pp. 83-86; vol. 1, No. 2; five pages.

Curtis et al.; "SMART—An Integrated Wireless System for Monitoring Unattended Patients"; J Am Med Inform Assoc.; Jan./Feb. 2008; pp. 44-53; vol. 15, No. 1.

Gao et al.; "Wireless Medical Sensor Networks in Emergency Response: Implementation and Pilot Results"; IEEE; 2008; pp. 187-192; IEEE.

Gao et al.; "A Pervasive, Real-Time Electronic Triage System with Noninvasive, Biomedical Sensors"; UCLA C.S. Dept Technical Report TR060030; Jan. 2007; pp. 1-11.

Harland et al.; "Electric potential probes—new directions in the remote sensing of the human body"; Measurement Science and Technology; 2002; pp. 163-169; vol. 13; IOP Publishing Ltd.

Harland et al.; "High resolution ambulatory electrocardiographic monitoring using wrist-mounted electric potential sensors"; Measurement Science and Technology; 2003; pp. 923-928; vol. 14; IOP Publishing Ltd.

Harland et al.; "Non-invasive Human Body Electrophysiological Measurements using Displacement Current Sensors"; International Workshop on Wearable and Implantable Body Sensor Networks; 2004; 3 pages.

Harland et al.; "Remote detection of human electroencephalograms using ultrahigh input impedance electric potential sensors"; Applied Physics Letters; Oct. 21, 2002; pp. 3284-3286; vol. 81, No. 17; American Institute of Physics.

Infrared Cameras, Inc.; product specification sheet; bearing a date of 2008; one page; located at www.infraredcamerasinc.com; Infrared Cameras Inc.

Jovanov et al.; "Patient Monitoring Using Personal Area Networks of Wireless Intelligent Sensors"; Biomed Sci Instrum.; 2001; pp. 373-378; vol. 37.

Kuo et al.; "Asymmetry in Sympathetic and Vagal Activities During Sleep-Wake Transitions"; Sleep; 2008; pp. 311-320; vol. 31, No. 3.

Lumidigm; Lumidigm Venus Series Multispectral Fingerprint Sensors; 2 pages; PDF created on Feb. 16, 2012; located at www.lumidigm.com.

Marzano et al.; "Slow Eye Movements and Subjective Estimates of Sleepiness Predict EEG Power Changes During Sleep Deprivation"; Sleep; 2007; pp. 610-616; vol. 30, No. 5.

Nakou et al.; "Pupillometry in depressed patients"; Annals of General Psychiatry; 2006; one page; vol. 5 (Suppl 1):S324; from International Society on Brain and Behavior: $2^{nd}$ International Congress on Brain and Behavior; Thessaloniki, Greece; Nov. 17-20, 2005.

Pace-Schott et al.; "The Neurobiology of Sleep: Genetics, Cellular Physiology and Subcortical Networks"; Nature Reviews Neuroscience; Aug. 2002; pp. 591-605; vol. 3; Nature Publishing Group.

Papadelis et al.; "Monitoring sleepiness with on-board electrophysiological recordings for preventing sleep-deprived traffic accidents"; Clinical Neurophysiology; 2007; pp. 1906-1922; vol. 118; Elsevier Ireland Ltd.

Papadelis et al.; "Indicators of Sleepiness in an ambulatory EEG study of night driving"; Proceedings of the $28^{th}$ IEEE EMBS Annual International Conference, New York City, USA, Aug. 30-Sep. 3, 2006; pp. 6201-6204; IEEE.

Pollock et al.; OSCAR-MDA An Artificially Intelligent Advisor for Emergency Room Medicine; 5 pages; printed on Oct. 18, 2011.

Pollock, John L.; "Cognitive Carpentry: A Blueprint for How to Build a Person"; 2 pgs. book description; published by the MIT Press on May 4, 1995; printed on May 1, 2012.

Prance et al.; "Adaptive Electric Potential Sensors for smart signal acquisition and processing"; Journal of Physics: Conference Series; 2007; 012025; pp. 1-5; vol. 76; IOP Publishing Ltd.

Rizzo et al.; "Chronic Vagus Nerve Stimulation Improves Alertness and Reduces Rapid Eye Movement Sleep in Patients Affected by Refractory Epilepsy"; Sleep; Jun. 27, 2003; pp. 607-611; vol. 26, No. 5.

Shaltis et al.; "Novel Design for a Wearable, Rapidly Deployable, Wireless Noninvasive Triage Sensor"; Proceedings of the 2005 IEEE; Engineering in Medicine and Biology $27^{th}$ Annual Conference; Shanghai, China, Sep. 1-4, 2005; pp. 3567-3570; IEEE.

Shi et al.; "MSMiner—a developing platform for OLAP"; Decision Support Systems, 2007; pp. 2016-2028; vol. 42; Elsevier B.V.

Tu et al.; "A Novel Electrochemical Microsensor for Nitric Oxide Based on Electropolymerized Film of o-Aminobenzaldehyde-ethylene-diamine Nickel"; Electroanalysis; 1999; pp. 70-74; vol. 11, No. 1; Wiley-VCH Verlag GmbH.

Warren et al.; "Designing Smart Health Care Technology into the Home of the Future"; Proceedings of the First Joint BMES/EMBS Conference Serving Humanity, Advancing Technology; Oct. 13-16, 1999, Atlanta, GA, USA; Abstract; p. 677; IEEE.

(56) References Cited

OTHER PUBLICATIONS

Williams et al.; "The Electronic Doctor (TED)—A Home Telecare System"; 18$^{th}$ Annual International Conference of the IEEE Engineering in Medicine and Biology Society, Amsterdam 1996; 1.1.5: Monitoring Instruments; pp. 53-54; IEEE.

Supplementary European Search Report; European App. No. EP 13 78 4623; Jan. 21, 2016 (received by our Agent on Jan. 18, 2016); pp. 1-2.

DEVICES, SYSTEMS, AND METHODS FOR AUTOMATED DATA COLLECTION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/463,945, entitled DEVICES, SYSTEMS, AND METHODS FOR AUTOMATED DATA COLLECTION, naming Mahalaxmi Gita Bangera, Michael H. Baym, Philip A. Eckhoff, Roderick A. Hyde, Muriel Y. Ishikawa, Elizabeth A. Sweeney and Lowell L. Wood, Jr. as inventors, filed 4 May 2012, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/463,975, entitled DEVICES, SYSTEMS, AND METHODS FOR AUTOMATED DATA COLLECTION, naming Mahalaxmi Gita Bangera, Michael H. Baym, Philip A. Eckhoff, Roderick A. Hyde, Muriel Y. Ishikawa, Elizabeth A. Sweeney and Lowell L. Wood, Jr. as inventors, filed 4 May 2012 now U.S. Pat. No. 9,317,662, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

Various embodiments are disclosed herein that relate to methods, devices, systems, and computer program products for automated data collection from a subject assessed for assigning a Queue Status Indicator depending on the subject's criticality state. Various embodiments include generating a Characteristic Value for a subject based on one or more characteristics or responses to one or more queries. Various embodiments include generating a Criticality Value based on comparison of the subject's Characteristic Value with a dataset (e.g., including values relating to other subjects, or the same subject, or an empty set). Various embodiments include determining a Queue Status Indicator based on the subject's Criticality Value. Various embodiments include generating a signal or other locational indicator of a particular subject who has been assigned a Queue Status Indicator.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
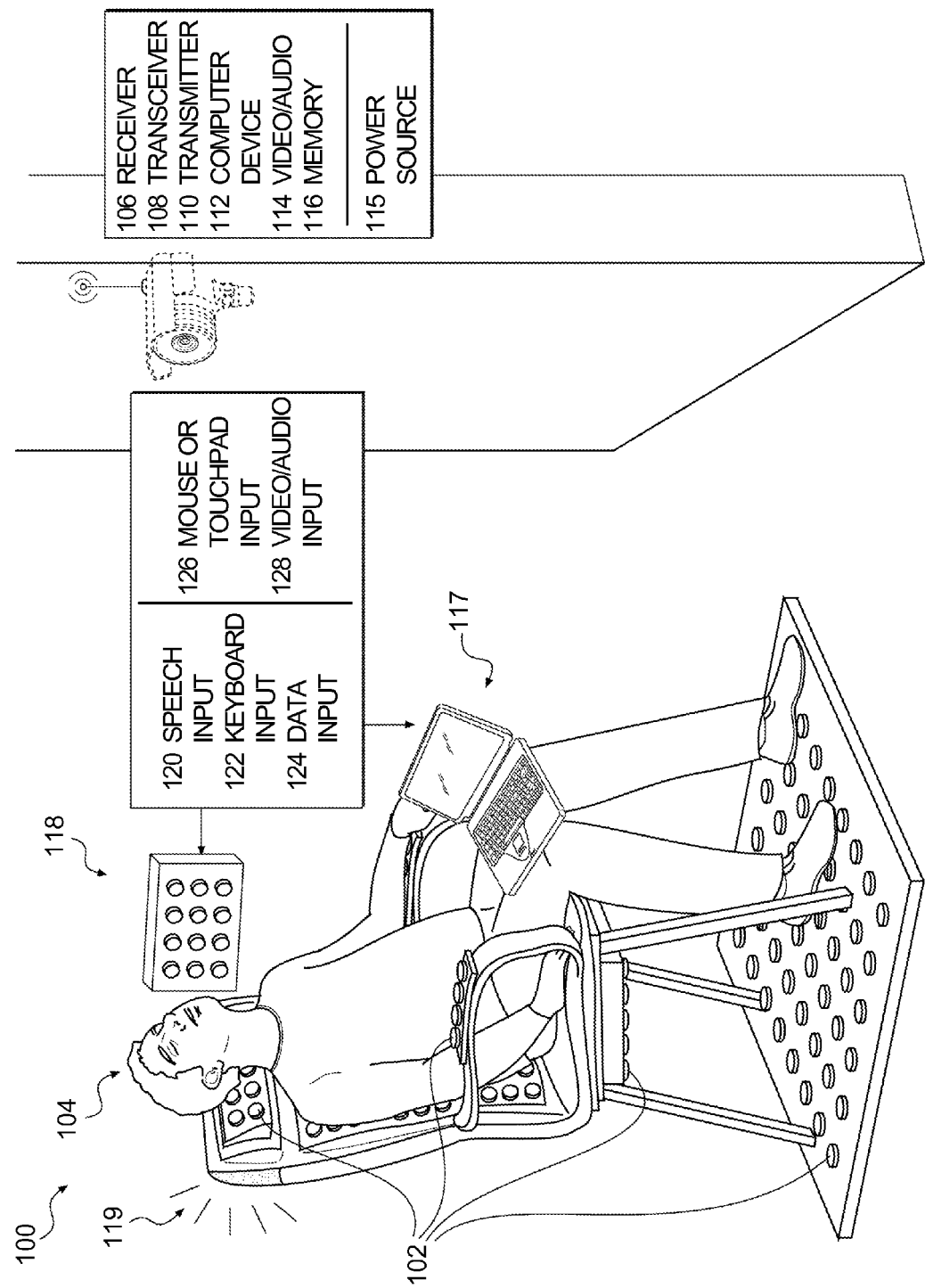
FIG. 1 illustrates a partial view of a particular embodiment described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In one embodiment, at least one of the methods, devices, computer systems, or computer program products disclosed herein is utilized for automated data collection (ADC) from a subject in a healthcare setting. In one embodiment, the methods, devices, computer program products, or computer systems disclosed herein assist in ranking the criticality of a subject in a healthcare (e.g., critical care or emergency room) setting and using the criticality of the subject to assign a Queue Status Indicator (QSI), which indicates the priority sequence for subjects in the queue awaiting medical attention. In one embodiment, the queue of subjects is updated in real time with one or more of temporal, spatial, or subject-specific data. In one embodiment, the methods, devices, computer systems, or computer program products save healthcare settings time, money, and reduce errors by increasing efficiency and collecting and presenting accurate information about each subject in the queue. Likewise, the methods, devices, computer systems, or computer program products provide benefits to subjects, including but not limited to, customized attention, higher priority ranking when warranted, and faster treatment. Thus, various embodiments disclosed herein assist healthcare facilities, particularly emergency departments, address quality of service and safety concerns. Further, the high level of data collection from the subject at the beginning results in fewer re-billing events for payment of services due to inaccurate information received, or mistakes made on intake of the subject to the healthcare facility.

In one embodiment, the methods, devices, computer systems, or computer program products also access any electronic health records that can include, among other things, the subject's past medical problems and/or treatments as well as possible identifying information.

In one embodiment, the subject includes a human. In one embodiment, the subject includes a healthcare worker. In one embodiment, the computer systems, devices, methods, computer program products determine whether a healthcare worker is well enough to go to work, enter a particular healthcare area, or perform a certain task. In one embodiment, the subject includes a healthcare patient. In one embodiment, the subject is a fetus. In one embodiment, the subject is a non-human animal. In one embodiment, the subject is a mammal, amphibian, fish, bird, or reptile. In one embodiment, the subject is a baby or child. In one embodiment subject is a geriatric. In one embodiment, the subject is a non-adult. In one embodiment, the subject is a cow, horse, dog, cat, or other domesticated animal.

In one embodiment, the systems, devices, methods, and computer program products described herein do not diagnose a subject. In one embodiment, the systems, devices, methods and computer program products described herein do not treat a subject, but rather assess the criticality of the subject. In one embodiment, the systems, devices, methods, and computer program products described herein rank the subject in sequential order when compared with other subjects in the queue, depending on the criticality of the subject's condition, as measured by an assessment, including among other things, one or more data collection questions (DCQs).

In one embodiment, a particular subject undergoes assessment with one or more sensors. For example, in one embodiment, the subject is assessed with one or more first sensors that then activates one or more second sensors, depending on the conditions sensed and criticality of the subject based on the first sensing (and optionally, consideration of information included in a subject's health record(s)) a first sensor initiates a system (e.g., a subject passes by it or enters the facility), or self-reporting of characteristics (e.g., symptoms) by the subject. In one embodiment, the subject undergoes assessment based on a decision tree originating with the first sensor and/or self-reporting of characteristics (e.g., symptoms) by the subject. (See for example, Shi et al., Science Direct pp. 2016-2028, Vol. 42 (2007); U.S. Patent App. Pub. No. 2010/0049095, the content of each is incorporated herein by reference.) For example, nonphysiologic and physiologic sensing can be performed by one or more sensors of the system alone or in conjunction with biological assays, which can be performed by the system (blood glucose finger prick test, breathalyzer, DNA swab, etc.), or self-reporting by the subject of any characteristics (e.g., symptoms) and of the subject's perceived severity or criticality of such characteristics (e.g., symptoms) (e.g., battery of questions or a figure of a human or other model subject for reporting the location of pain or other trouble) in order to generate one or more Characteristic Values for the subject. In an embodiment, the subject is unaware of the assessment with one or more sensors. In an embodiment, the subject is unresponsive or unconscious. In an embodiment, the subject is given a choice as to whether to be assessed by the one or more sensors.

Next, depending on the results of the assessment (i.e., sensed conditions, biological assays, self-reported characteristics, and optionally the subject's health record(s) (e.g., electronic health record)), and the corresponding Characteristic Values for the subject, based on comparison with a characterization value dataset. Once the Characteristic Values for the subject are generated, the subject is assigned a Criticality Value based on comparison with the criticality value dataset. In one embodiment, sensed, assayed, or reported characteristics are compared with known values, including but not limited to a database of standardized values, or a subject's own health history values. Based on the Criticality Value of the subject, a decision is made utilizing instructions implemented on a computing device (network, etc.) to initiate a second set of sensors, biological assays, or data collection questions (DCQs). The second assessment can be predetermined or customized for a particular subject, depending on the needs of the healthcare facility or the needs of the subject. In an embodiment, the subject's Criticality Value is compared with the Criticality Value dataset including the Criticality Values previously generated for subjects in the queue. In one embodiment, the subject's present Criticality Value is compared with the Criticality Value dataset including Criticality Values previously generated for the subject based on his or her own health history.

For example, if it is detected or self-reported that a subject has a fever and elevated heart rate, the information from the subject's health record (or information from friends/relatives that are with the subject) can be considered in order to determine which immunizations the subject has or has not received. This may prompt a DCQ of asking the subject if he/she has traveled anywhere recently, or been in close proximity to someone who has. This may also illicit further sensors to sense additional characteristics or the system to perform biological assays (e.g., finger prick for blood test with PCR for pathogens, etc.) and evaluate the overall condition of the subject based on the sensed conditions. If further sensors or biological assays indicate that the subject has no other symptoms, for example, this finding will reduce the overall Criticality Value of the subject and will assign a Queue Status Indicator accordingly.

In one embodiment, at least one first sensor or other components of the system is in operable communication with at least one second sensor or other component. In an embodiment, the at least one first sensor or other component is in wireless communication with at least one second sensor or other component. Various modes of wireless communication are described herein. In one embodiment, information obtained or collected regarding the subject is shared or transferred from one part of the system to another. For example, the results of an assay can be entered into the subject's medical records, or the subject's health records can direct the focus of a sensor for assessing the subject's present state of health. In this way, in an embodiment, the system represents an integrated system of multi-directional communication between a subject, a healthcare worker, one or more databases, and one or more assays, sensors, or self-reporting queries.

In one embodiment, at the time the subject first enters the healthcare facility, he or she can refuse to have any data collected by way of assessment (e.g., sensors, biological assays, health record (including prescription records, stored electronic monitoring data, etc.), family health history (including questioning family members), or DCQs). In such a situation, for example, the subject may still provide a fingerprint, driver's license, social security number, birth date, anonymous unique identifier, or other form of identification for check-in, and optional accessing of the subject's health records. In one embodiment, a date and/or time stamp is registered at the time the subject checks in or begins the assessment process. In one embodiment, if two subjects would otherwise be assigned the same QSI, the date or time stamp that is earlier in time will trump the later in time subject. In this way, two subjects with the same level of criticality will be seen in the order in which they arrived at the healthcare facility.

In one embodiment, the systems, devices, methods, or computer program products described herein include the ability to interact with additional information from, for example, another computer system of dataset (e.g., personal data storage, personal monitoring device or sensor network, patient tracking system (e.g., Amerlior EDTracker), information system (e.g., Amelior ED), network sensors (e.g., mT Tag™ or other network sensor), implanted sensors, or user input. See for example, U.S. Patent App. Pub. Nos. 2007/0088713, and 2006/0212085, each of which is incorporated herein by reference.

In one embodiment, the systems, devices, methods, or computer program products described herein include access to the subject's health history (e.g., individual and/or family health history). In one embodiment, the systems, devices, methods, or computer program products use artificial intelligence for at least one step of the described embodiment(s) (e.g., OSCAR-MDA, CodeBlue, etc.).

In one embodiment, the systems, devices, methods, or computer program products described herein include interaction or tracking information with other datasets, for example, a public health database (e.g., CDC, NIH, state or local agency database, etc.). In one embodiment, the systems, devices, methods, or computer program products described herein access and interact with infectious disease information, bio-weapon or chemical weapon information (e.g., Homeland Security), adverse effects of drugs or equipment (e.g., for manufacture recalls), or healthcare facility statistics (e.g., infection rates, hygiene, liability, etc.). In one embodiment, a decision may be made based at least partly on information received from such a database, that the subject must be quarantined. In one embodiment, information is transferred one or more directions, including updating databases with infectious disease or other public health issues (signs of bio/chemical weapons), adverse effects to drugs or equipment (e.g., for recalls), hospital issues such as infection rates, hygiene, or liability.

In one embodiment, the Criticality Value of the subject, or one or more Characteristic Values, satisfies a threshold condition, and optionally indicates that one or more Characteristic Values of the subject must be monitored. For example, the subject can be monitored continuously or intermittently (e.g., at predetermined times or customized times) based on the subject or subject's condition.

In one embodiment, one or more sensors utilized in assessing the subject, including one or more remote non-conductive sensors, are located in one or more of furniture, wall, floor, door, doorway, reception counter, pen, computer monitor or other hardware, or computing device from which a subject is self-reporting one or more characteristics (e.g., symptoms). In one embodiment, the one or more sensors are included in an exam table, chair armrest, gurney, or other furniture.

In one embodiment, the one or more sensors include at least one of ultrasound, bioimpedance, or infrared thermometry. In one embodiment, the one or more sensors include audio sensors (e.g., cameras that are audio and/or video recorders), or eye tracking (e.g., imagers). See, for example, U.S. Patent App. Pub. Nos. 2010/0049095; 2006/0190419; 2008/0039698; or 2010/0174533, or U.S. Pat. No. 6,475,161, each of which has been incorporated herein by reference.

In one embodiment, one or more subject specific characteristics are measured, including but not limited to characteristics of the subject including at least one of height, weight, fingerprint, facial features, visible physical malformations, eye characteristic, appearance of skin, appearance of hair, appearance of nails, respiratory sounds, body temperature, blood gas level, heart rate, brain electrical activity, respiration rate, facial expression, blood chemistries, blood cell counts, platelet counts, antibody titer, calcium level, blood antigen type, tissue antigen type, evidence of a pathogen exposure, lipids levels, perception of pain level, body movement, gait, stiffness, evidence of cognition state, dehydration, self-reported pain, self-reported malaise, self-reported injury, self-reported event, rigor, fever, self-reported light-headedness or dizziness, self-reported dry mouth, self-reported nausea, self-reported shortness of breath, self-reported thirst, weakness, self-reported sleepiness, hearing loss or problem, vision loss or problem, self-reported constipation or diarrhea, flatulence, self-reported urinary incontinence, self-reported loss of smell or problem, self-reported loss of voice or problem, self-reported loss of taste, self-reported loss of ability to walk, self-reported loss of ability to write, self-reported loss of ability of limb or digit use, or other characteristic. For example, the appearance of skin, hair, or nails can be evaluated by standard criteria, including but not limited to hair loss or change in condition, change in any birthmarks, tattoos or skin blemishes (or arise of any new birthmarks, moles, or other skin marks), body odor, change in nail condition, damage due to exposure to sun or chemicals, etc.

In one embodiment, one or more subject specific characteristics are assessed by one or more direct or indirect sensors (e.g., remote non-conductive sensors). In one embodiment, one or more subject specific characteristics are assessed by self-reporting by the subject. For example, in one embodiment, the subject interacts with at least one input/output computing device (e.g., kiosk, tablet, desktop, laptop, handheld device, etc.) and responds to data collection questions (DCQs) relating to his or her characteristics (e.g., symptoms). For example, in one embodiment, the subject may be presented with (in any number of different possible languages) DCQs relating to one or more characteristics of: abdominal pain, knee pain, blood in stool, low back pain, chest pain, nasal congestion, constipation, nausea or vomiting, cough, neck pain, diarrhea, numbness or tingling in hands or feet, difficulty swallowing, pelvic pain (female or male), dizziness, eye discomfort and/or redness, shortness of breath, foot or ankle pain, shoulder pain, foot or leg swelling, sore throat, headache, urinary problems, vision problems, heart palpitations, hip pain, wheezing, joint or muscle pain, skin rash or other rash, earache, or other symptoms.

In one embodiment, the DCQs asked of the subject are directed based on previous answers provided or other information known about the subject (e.g., by way of the self-reporting, or by way of electronic health record, sensed information, etc.). For example, the DCQs may be different based on the person's gender, health history, or response to answering a first round of specific DCQs. In one embodiment, the DCQs are prioritized, for example, with the first DCQ has a heavy weight assigned due to its criticality, and depending on the response to the DCQ, the DCQs that follow are tailored to address the concerns presented in the prior response.

For example, if a subject with a history of heart disease enters the healthcare facility, and a first remote non-conductive sensor senses and signals that the subject has an irregular heartbeat, a second sensor quickly determines if the subject is responsive enough to answer DCQs. If so, one of the first DCQs for this subject could be: "Do you have chest pain?" If the subject responds, "Yes," then a second DCQ could be, for example: "Rank your level of pain on a scale of 1 to 5, with 5 being greatest level of pain." Again, depending on the response, with each DCQ receiving a particular numerical Characteristic Value, the DCQs will be adjusted specifically for the reporting subject. For example, if the subject reports a high level of pain "5," the system will determine that the subject has a high Characteristic Value, and when compared with the Characteristic Value dataset, generates a Criticality Value, which in turn is assigned a high Queue Status Indicator (QSI). The subject's QSI is determined by comparing the subject's Criticality Value with the Criticality Value dataset, including Criticality Values from subjects in the queue, if any, or Criticality Values from this particular subject, based on his or her own health history. When one or more Characteristic Values or Criticality Value(s) satisfy a threshold condition, the subject is awarded a higher QSI, potentially moving him to be first in line to receive medical attention. In the event that the subject's one or more Characteristic Values or Criticality Value(s) satisfy a threshold condition, the subject may receive an alert that indicates he or she will continue to be monitored (e.g., by one or more sensors, DCQs, or other means), and is continually assessed for changes. If the subject's health condition is both critical and unstable, for example, a location indicator is immediately activated in order to identify the location of the subject within the healthcare facility.

However, in the same example, if the subject responds, "No," to the first DCQ of "Do you have chest pain?" Then a second DCQ could be: "Do you feel dizzy or lightheaded?" If the subject responds, "No," the subject's responses are assigned a lower Criticality Value than in the first scenario. However, the subject may still receive a high QSI based on his history of heart disease and presentation of heart palpitations. In this case, the subject would still continue to be monitored by one or more sensors for any change in condition, which could result in a change in QSI based on the Criticality Value of any changed assessment measurements.

In one embodiment, the information input from the subject is assigned varying degrees of confidence depending on the source of the information, in order to reduce conflicting information. For example, if a subject self-reports a high level of pain, but sensors detect no corresponding characteristics typical of a high level of pain (e.g., rapid heart rate, perspiration, agitation, facial expressions of discomfort, etc.), the self-reported Characteristic Value of a high level of pain may receive a lower numerical value than if the one or more sensors verify characteristics typical of a subject's being in a high level of pain.

In one embodiment, exemplary DCQs include but are not limited to, "Do you smoke?"; "Do you have any allergies?"; "Do you have any changes in skin or hair?"; "Do you have shaking or tremors?"; "Do you have numbness anywhere in your body?": "Have you traveled lately?"; "Do you have difficulty swallowing?"; "Have you ever had a fainting spell or convulsion?"; "Do you have any lumps or bumps in your body?"; "Please indicate whether you are male or female."; "Are you pregnant?"; "Any change in appetite?"; "Are you sexually active?"; "Do you have any vomiting?"; "Do you drink alcohol?"; "List any drugs ingested in the past 24 hours, including recreational or pharmaceutical drugs."; "Have you had any medical biological assays or treatments (including surgeries) lately?"; "Rate your pain on a scale of 1 to 5, with 5 being the highest amount of pain you have ever had."; "How is your energy level?"; "Are you socially withdrawn?"; "Have you been feeling anxious lately?"; etc. Further examples of potential questions are available, for example, in U.S. Pat. App. Pub. No. 2004/0138924, which is incorporated herein by reference.

In one embodiment, if two or more subjects would be assigned the same QSI based on each of their Criticality Values, respectively, then a date/time stamp from the initial check-in of the subject at the healthcare facility will determine which subject receives a higher priority QSI, with the subject presenting earlier in time receiving the higher QSI. In one embodiment, as described elsewhere herein, if one or more Characteristic Values of a subject changes, the system will update the dataset and the subject's QSI may change, depending on the QSI and condition of the other subjects in each dataset. Thus, in one embodiment, the dataset is dynamic (Characteristic Value dataset, Criticality Value dataset, Queue Status Indicator dataset) in that it is updated when new data is collected for a new subject entering the queue, and/or it is updated when the status changes of a subject already in the queue. In one embodiment, the corresponding dataset will update based on the subject's changed status, which will in turn update each dataset accordingly. For example, if one or more Characteristic Values of a subject are being monitored and one or more change, then the subject's Criticality Value will change accordingly. When compared with the Criticality Value dataset, the subject's Queue Status Indicator will change to correspond with the change in the subject's Criticality Value.

As another example, a subject enters the waiting room, activating a sensor (subject can be responsive or unresponsive). The subject is immediately assigned a unique identifier and is remotely scanned for vital signs, and a full image scan is taken.

At least a portion of the image is compared to various parameters and databases for signs of trauma, evaluation of appearance (skin, hair, nails, etc.), movement and cognition. At least a portion of the image is optionally compared with medical history by way of facial recognition. In such a case, a subject then enters the queue based on its Characteristic Values reflected by the Criticality Value which generates the Queue Status Indicator.

Once the subject has been placed in the queue, additional scans are initiated, including EEG for possible schizophrenia or determination of level of consciousness. For example, a dedicated camera or other dedicated equipment is used for sensing level of consciousness or alertness.

As shown in FIG. 1, the system 100 includes at least one input/output device 117, or the head sensor 118, can each include data input 124, keyboard input 122, mouse or touchpad input 126, speech input 120, or audio/video input 128. As indicated, one or more sensors 102, 118, are located in proximity to or in directly contact with the subject 104. The optional location indicator 119, allows for notification of the subject with the highest Criticality Value, translated into the highest QSI. As indicated, in an embodiment, the input/output device (including a keyboard, audio/video, or other device) includes a receiver 106 (optionally wireless, shown on camera), transceiver 108 (optionally wireless), transmitter 110 (optionally wireless), includes audio/video capabilities 114, includes a power source 115, and memory 116. In an embodiment, the input/output device 117 is operably coupled to a computer device 112.

In one embodiment, the ADC system includes circuitry having one or more components operably coupled (e.g., communicatively, electromagnetically, magnetically, ultrasonically, optically, inductively, electrically, capacitively coupled, or the like) to each other. In one embodiment, circuitry includes one or more remotely located components. In one embodiment, remotely located components are operably coupled via wireless communication. In one embodiment, remotely located components are operably coupled via one or more receivers 106, transceivers 108, or transmitters 110, or the like.

In one embodiment, circuitry includes, among other things, one or more computing devices such as a processor (e.g., a microprocessor), a central processing unit (CPU), a digital signal processor (DSP), an application-specific integrated circuit (ASIC), a field programmable gate array (FPGA), or the like, or any combinations thereof, and can include discrete digital or analog circuit elements or electronics, or combinations thereof. In one embodiment, circuitry includes one or more ASICs having a plurality of predefined logic components. In one embodiment, circuitry includes one or more FPGA having a plurality of programmable logic components.

In one embodiment, circuitry includes one or more memory devices 116 that, for example, store instructions or data. For example in one embodiment, the automated data collection system 100 includes one or more memory devices 116 that store information related to one or more characteristics of the subject that has been assessed, electronic health records, self-reported symptoms, insurance, or other health-related information. Non-limiting examples of one or more memory devices 116 include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like, persistent memory or the like, Erasable Programmable Read-Only Memory (EPROM), flash memory, or the like. The one or more memory devices 116 can be coupled to, for example, one or more computing devices 112 by one or more instructions, data, or power buses.

In one embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In one embodiment, circuitry includes one or more user input/output components that are operably coupled to at least one computing device to control (electrical, electromechanical, software-implemented, firmware-implemented, or other control, or combinations thereof) at least one parameter associated with, for example, the health information related to the subject's health condition.

In one embodiment, the system is configured to operate in an application service provider format. In one embodiment, the system is configured to be implemented using open source tools. For example, in one embodiment, the system includes using one or more of Java, Java server pages (JSP), Java database connectivity (JDBC), structured query language (SQL), extensible markup language (XML), user interface language (XUL) and/or scalable vector graphics (SVG) technologies.

In one embodiment, image-based applications such as viewers and/or toolkits (e.g., Insight Segmentation and Registration Toolkit (ITK)), are incorporated for further intake of information. In one embodiment, CAD implementations or image segmentation may allow previous processing of images previously accepted on intake of information from the subject.

In one embodiment, circuitry includes a computer-readable media drive or memory slot that is configured to accept non-transitory signal-bearing medium (e.g., computer-readable memory media, computer-readable recording media, or the like). In one embodiment, a program for causing a system to execute any of the disclosed methods can be stored on, for example, a computer-readable recording medium (CRMM), a non-transitory signal-bearing medium, or the like. Non-limiting examples of signal-bearing media include a recordable type medium such as magnetic tape, floppy disk, a hard disk drive, Compact Disc (CD), a Digital Video Disk (DVD), Blu-Ray Disc, digital tape, computer memory, or the like, as well as transmission type medium such as a digital and/or analog communication medium (e.g., fiber optic cable, waveguide, wired communications link, wireless communication link (e.g., receiver 106, transceiver 108, or transmitter 110, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, cloud, or the like. In one embodiment, the ADC system 100 includes circuitry having one or more modules optionally operable for communication with one or more input/output components that are configured to relay user output/input. In one embodiment, a module includes one or more instances of electrical, electromechanical, software-implemented, firmware-implemented, or other control devices. Such devices include one or more instances of memory, computing devices, antennas, power or other supplies, logic modules or other signaling modules, gauges or other such active or passive detection components, piezoelectric transducers, shape memory elements, micro-electromechanical systems (MEMS) elements, or other actuators.

In one embodiment, the computing device further includes audio/visual input/output connected to the system and configured to interact with the subject. In one embodiment, the system further includes a printing device connected to the computing device. In one embodiment, the system includes an input/output device including a graphical interface (e.g., display, touch screen, etc.).

In one embodiment, the one or more sensors include, for example, one or more acoustic sensors, optical sensors, electromagnetic energy sensors, image sensors, photodiode arrays, charge-coupled devices (CCDs), complementary metal-oxide-semiconductor (CMOS) devices, transducers, optical recognition sensors, infrared sensors, radio frequency component sensors, thermo sensors, three-dimensional sensors (e.g. to assess the subject's facial expressions exhibiting pain or discomfort, flushing or redness, or a subject's gait or other movements, etc.).

In one embodiment, one or more components of the system (e.g., chair impregnated with sensors for assessing one or more characteristics of the subject) operate in a networked environment using logic connections to one or more remote computing devices (e.g., a common network node, a network computer, a network node, a peer device, a personal computer, a router, a server, a tablet PC, a tablet, etc.) and typically includes many or all of the elements described above. In one embodiment, the logic connections include connections to a local area network (LAN), wide area network (WAN), and/or other networks. In one embodiment, the logic connections include connections to one or more enterprise-wide computer networks, intranets, and the internet. In one embodiment, the system 100, the one or more components of the system, or the like operate in a cloud computing environment including one or more cloud computing systems (e.g., private cloud computing systems, public cloud computing systems, hybrid cloud computing systems, or the like).

In one embodiment, the subject 104 includes a fetus. In one embodiment, the subject includes a human being. In one embodiment, the human being includes a fetus. In one embodiment, the subject includes a living organism that is distinguished from plants by independent movement and responsive sense organs.

In one embodiment the one or more sensors 102 may sense heartbeat intervals and ECG readings remotely by measuring small electrical potentials using a high input impedance electrometer. An example of such a sensor device is described in U.S. Patent Application Pub. No. 2006/0058694, supra; WO 2003/048789, supra; Harland, Meas. Sci. Technol., supra; Prance, 2007 Journal of Physics: Conference Series, supra, each of which is incorporated herein by reference. Such sensor devices are expected to provide noninvasive and remote monitoring. In one embodiment, the one or more sensors 102 may be worn by the subject in or on clothing or jewelry, such as in wrist bands, and may be in non-conductive contact with the body. For example, as described by U.S. Patent Application Pub. No. 2006/0058694, supra; WO 2003/048789, supra; C. J. Harland et al., *High resolution ambulatory electrocardiographic monitoring using wrist-mounted electric potential sensors*, 14 Meas. Sci. Technol. 923-928 (2003), each of which is incorporated herein by reference. In one embodiment, the one or more sensors 102 may be included in or associated with a piece of furniture, such as a chair or desk, or electronics such as a personal computer, or with some other remote item within, e.g., within approximately one meter from the subject. In one embodiment, the one or more sensors 102 are able to measure electric potentials may be embedded in objects, such as a bed or chair, in direct but non-conductive contact with the subject. For example, as described by U.S. Pat. No. 7,245,956, supra, each of which is incorporated herein by reference. In one embodiment, the one or more sensors 102 may sense heartbeat intervals and electrocardiographic information by examining physiologic activity of the subject or its organs and may be operable to sense a characteristic of the subject 104 in response to an electromagnetic signal sent at or illuminating the subject and reflected from the subject. In one embodiment, the illuminating may include exposing, subjecting, or directing energy at the subject. Systems using illuminating or reflected electromagnetic signals, including radiofrequency (RF) or microwave signals, are described in U.S. Pat. No. 7,272,431; U.S. Patent Application Pub. No. 2004/0123667; or U.S. Patent Application Pub. No. 2008/0045832; each of which is incorporated herein by reference. In one embodiment, one or more sensors 102, which may be or include a sensor array, may be deployed, for example, throughout a room, perhaps as part of a smart room network, so as to monitor the subject at rest or in motion.

In one embodiment, information gathered by the one or more sensors 102 may be communicated to a computer. In one embodiment, information may be communicated to a computer of the system electronically. In one embodiment, information may be communicated to a computer of the system wirelessly, for example using radio waves or ultrasound waves, or Bluetooth™ technology. In one embodiment, a computer, may be used to process the information. The computer may be part of a network.

FIG. 1 illustrates one embodiment in which a system 100, includes one or more sensors 102 configured to assess a subject 104. As shown, the subject 104, can be assessed by various modes, including but not limited to, input/output device (e.g., user interface) 117, head sensor (e.g., breathalyzer, thermal scan, respiration sensor, pupillometry, retinal scan, etc.) 118, audio/visual device 114 (e.g., camera), optionally including one or more of a receiver 106, transceiver 108, transmitter 110, computer device 112, memory 116, or power source 115. As shown, in one embodiment, an audio or visual criticality indicator 119 signals a subject whose Criticality Value satisfies a threshold condition (e.g., satisfying an emergency or critical threshold), based, for example, on assessed characteristics of the subject, self-reporting symptoms, and/or health history records.

In one embodiment, the one or more sensors 102 includes a sensor array configured to sense a characteristic of the subject 102 without physically contacting the subject. For example, the sensor array may include at least two sensor heads. In one embodiment, the at least two sensor heads may include at least two sensor heads configured to sense the same characteristic of the subject. In one embodiment, the at least two sensor heads may include sensor heads configured to sense different characteristics of the subject. For example, one sensor head may be configured to sense temperature, another sensor head configured to sense heart rate, and a further sensor head configured to sense blood pressure. In one embodiment, the sensor includes a sensor responsive, without physically contacting the subject, to an impedance, capacitance, permittivity, reflectivity, absorption, or electrical activity of the subject. For example, a sensor including a capacitive proximity sensor element configured to sense a characteristic of a subject without physically contacting the subject is described in U.S. Patent Application Pub. No. 2008/0246495, incorporated herein by reference. For example, in one embodiment, a reflection or reflectivity characteristic may include an acoustic, light, or radio wave reflectivity. In one embodiment, the sensor includes a sensor responsive to the characteristic of a subject without physically contacting the subject. In one embodiment, the sensor includes a sensor configured to sense a characteristic of a subject, for example, at least one anatomical or physiological characteristic. The characteristics measured include steady state characteristics (e.g., height, weight, etc.), and variable characteristics (e.g., heart rate, blood oxygen level, etc.).

In one embodiment, the one or more sensors 102 includes a sensor configured to sense a characteristic of the subject 104 without physically contacting the subject. For example, the sensor may be configured for an association with a chair, a pillow, or a gurney. In one embodiment of this sensor, the sensor may include a sensor configured for a physical association with an article of clothing or garment wearable by a subject and to sense a characteristic of the subject without physically contacting the subject. In one embodiment of this sensor, the sensor may include a sensor configured for a physical association with an object wearable by a subject and to sense a characteristic of the subject without physically contacting the subject. For example, the sensor may be configured for a physical association with eye glasses or jewelry. For example, a sensor configured for a physical association with an object wearable by a subject is described by U.S. Patent Application Pub. No. 2006/0058694, Electrodynamic sensors and applications thereof, to T. Clark et al.; WO 2003/048789, Electrodynamic sensors and applications thereof, by T. D. Clark et al.; or C. J. Harland et al., *High resolution ambulatory electrocardiographic monitoring using wrist-mounted electric potential sensors*, 14 Meas. Sci. Technol. 923-928 (2003), each of which is incorporated herein by reference.

In one embodiment, the one or more sensors 102 include a sensor device configured to sense a characteristic of the subject 104 without physically touching the subject. In one embodiment, the sensor device includes a sensor device configured to sense a characteristic of a subject without a resistive contact with the subject. In one embodiment, the sensor device includes a sensor device configured to sense a characteristic of a subject without an electrically conductive contact with the subject. In one embodiment, the sensor device includes a sensor device configured to sense a characteristic of a subject across a non-electrically conductive gap with the subject.

In one embodiment, the sensor device includes an electrodynamic sensor device configured to sense an electrical activity of the heart of a subject without physically contacting the subject. For example, the electrodynamic sensor may be configured to sense a heart rate, electrical activity of the heart, such as electrocardiography (ECG), or conductivity. An example of a high input impedance electrodynamic sensor device configured to sense an electrical activity of a heart of a subject without physically contacting the subject is described in U.S. Patent Application Pub. No. 2006/0058694; WO 2003/048789, supra; Electrodynamic sensors and applications thereof, to T. Clark et al. In one embodiment, the sensor device includes an adaptive electric potential sensor device configured to sense a characteristic of a subject without physically contacting the subject. An example of an adaptive electric potential sensor device configured to sense a characteristic of a subject without physically contacting the subject is described in R. L. Prance et al., *Adaptive Electric Potential Sensors for smart signal acquisition and processing*, 76 Journal of Physics: Conference Series, 012025 (2007). In one embodiment, the sensor device includes an electric potential probe sensor device configured to sense a characteristic of a subject without physically contacting the subject. An example of an electric potential probe sensor device configured to sense a body electrical activity or signals, such as for example arterial pulse or other body electrodynamics, of a subject without physically contacting the subject is described in C. J. Harland et al., *Electric potential probes—new directions in the remote sensing of the human body*, 13 Meas. Sci. Tech. 163-169 (2002).

In one embodiment, the one or more sensors 102 include a sensor configured to sense at least one of an electrical, acoustic, thermal, radiative, absorption, reflection, gaseous emission, or transmissibility characteristic of the subject. In one embodiment, a thermal characteristic may include an infrared measured thermal characteristic. In one embodiment, a thermal characteristic may include microwave length (3-30 cm) electromagnetic radiation naturally emitted by the subject. For example, a sensor configured to sense a thermal characteristic of the subject includes a microwave radiometer operable to measure natural electromagnetic radiation from the subject's internal tissue in the microwave range. In one embodiment, the microwave radiometer may be combined with an infrared sensor as described in R. Avagyan et al., *New diagnostic methods in acupuncture*, ICMART '99 International Medical Acupuncture Symposium 7, Riga, (May 21-23, 1999), each of which is incorporated herein by reference. See also, Pub. No. WO 2006/091123 (PCT/RU2006/000072), each of which is incorporated herein by reference. For example, a transmissibility characteristic may include a light or radio wave transmissibility characteristic. For example, in one embodiment, a radiative characteristic may include gammas or other types of radiation emitted by the body of the subject itself, for example potassium 40. An embodiment of a gamma-ray sensor device configured to sense a characteristic of a subject without physically contacting the subject is expected to be provided by the Radtell™ passive gamma-ray sensor by Oak Ridge National Laboratory of Oak Ridge, Tenn.

In one embodiment, a sensor 102 is operably coupled to one or more sensor control units 134. In one embodiment, the one or more sensor control units 134 serve to regulate the activity of the one or more sensors 102. For example, in one embodiment, one or more sensor control units 134 regulate one or more times when the one or more sensors 102 detect one or more signals from the subject that are related to one or more characteristics of the subject. In one embodiment, the one or more sensor control units 134 regulate one or more time periods when one or more sensors 102 detect one or more signals from the subject that are related to one or more characteristics of the subject. In one embodiment, one or more sensor control units 104 are operably coupled to one or more detection processors 136.

In one embodiment, a sensor 102 is configured to wirelessly communicate sensed electrical signals originating from a subject. In one embodiment, a sensor 102 is electrically or optically coupled to the control circuitry to communicate the one or more signals thereto.

In one embodiment, a sensor 102 includes one or more sensor housings 138. In one embodiment, one or more sensor housings 138 are operably coupled with one or more detectors 136.

In one embodiment, numerous types of detectors 136 may be operably coupled to the one or more sensors 102. In one embodiment, the one or more sensors include at least one detector and reporter. In one embodiment, numerous different types of detectors 136 are operably coupled to one or more sensors 102. Examples of such detectors 136 include, but are not limited to, electrodes, surface plasmon resonance detectors, microelectromechanical systems detectors, microcantilever detectors, nitric oxide detectors, osmotic detectors, relativity-based detectors, chemical detectors, pressure detectors, electrochemical detectors, piezoelectric detectors, pH detectors, hydrogel detectors, enzymatic detectors, ball integrated circuit detectors, affinity viscosimetric detectors, blood pressure detectors; metal detectors, glucose detectors, and the like (e.g., U.S. Pat. Nos. 7,162,289; 6,280,604; 5,603,820; 5,582,170; 6,287,452; 7,291,503; 6,764,446; 7,168,294; 6,823,717; 7,205,701; 6,268,161; 4,703,756;

6,965,791; 6,546,268; 6,210,326; 6,514,689; 6,234,973; 6,442,413; Tu et al., Electroanalysis, 11:70-74 (1999), each of which is incorporated herein by reference). In one embodiment, one or more detectors 136 are configured to detect one or more of pH, chemicals, or nerve signals from the subject.

In one embodiment, one or more sensor housings 144 include circuitry that is operably coupled to one or more detectors 136. In one embodiment, one or more sensor housings 144 include circuitry that is configured to facilitate elimination of one or more sacrificial layers. In one embodiment, one or more sensor housings 144 include circuitry that is configured to be operably coupled to one or more sensor control units 134. In one embodiment, one or more sensor housings 144 include circuitry that is configured to be operably coupled to one or more sensor power sources 115. In one embodiment, one or more sensor housings 144 include circuitry that is configured to be operably coupled to one or more sensor receivers 106. In one embodiment, one or more sensor housings 144 include circuitry that is configured to be operably coupled to one or more sensor transmitters 110.

In one embodiment, a sensor 102 includes one or more sensor power sources 115 (including but not limited to batteries). In one embodiment, a sensor 102 is operably coupled to one or more sensor batteries 115. In one embodiment, a sensor battery 115 includes a thin-film fuel cell such as a solid oxide type (SOFC), a solid polymer type (SPFC), a proton exchange membrane type (PEMFC), and/or substantially any combination thereof. Methods to fabricate such thin-film fuel cells are known and have been described (e.g., U.S. Pat. No. 7,189,471, incorporated herein by reference). In one embodiment, one or more sensor batteries 115 include one or more storage films that are configured for energy storage and energy conversion. Methods to fabricate such storage films are known and have been described (e.g., U.S. Pat. No. 7,238,628, incorporated herein by reference). In one embodiment, a sensor battery 115 is a biobased battery (e.g., U.S. Pat. No. 6,994,934, incorporated herein by reference). In one embodiment, one or more sensor batteries 115 are thin-film batteries. Methods to fabricate thin-film batteries, including thin film microbatteries, are known and have been described (e.g., U.S. Pat. Nos. 5,338,625, 7,194, 801; 7,144,655; 6,818,356, incorporated herein by reference). In one embodiment, one or more sensor electromagnetic receivers (not shown) are used to electromagnetically couple power to energize one or more sensors 102 from an external power source 115. Methods to construct electromagnetic receivers have been described (e.g., U.S. Pat. No. 5,571,152), incorporated herein by reference. In one embodiment, the receiver and/or transmitter are not part of the sensor.

In one embodiment, the system 100 includes one or more sensor transmitters 110. Numerous types of transmitters 110 can be used in association with system 100. Examples of such transmitters 110 include, but are not limited to, transmitters that transmit one or more acoustic signals, optical signals, radio signals, wireless signals, hardwired signals, infrared signals, ultrasonic signals, and the like (e.g., U.S. Pat. Nos. RE39,785; 7,260,768; 7,260,764; 7,260,402; 7,257,327; 7,215,887; 7,218,900), each of which is incorporated herein by reference. In one embodiment, one or more sensor transmitters 110 may transmit one or more signals that are encrypted. Numerous types of transmitters are known and have been described (e.g., U.S. patent Nos. and Published U.S. patent applications: U.S. Pat. Nos. 7,236,595; 7,260,155; 7,227,956; US2006/0280307), incorporated herein by reference.

In one embodiment, the system 100 includes one or more sensor receivers 106. Numerous types of sensor receivers 106 may be used in association with system 100. Examples of such sensor receivers 106 include, but are not limited to, receivers that receive one or more acoustic signals, optical signals, radio signals, wireless signals, hardwired signals, infrared signals, ultrasonic signals, and the like. Such receivers 106 are known and have been described (e.g., U.S. Pat. Nos. RE39,785; 7,218,900; 7,254,160; 7,245,894; 7,206, 605), incorporated herein by reference.

In one embodiment, the system includes at least one computing processor that utilizes at least one set of instructions derived from mathematical trends such as queuing theory. For example, the theory of mathematical queuing allows for derivation and calculation of several performance measures including the average wait time in the queue or the system, the expected number waiting or receiving service, and probability of encountering the system in various states (e.g., empty, full, having an available server or having to wait a certain amount of time to be served). In addition, useful queuing modeling can be based on the Poisson process and its companion exponential probability distribution, which mimics the response of the system being modeled to those same inputs.

Various statistical programs or computer algorithms for simulating systems may be implemented with various embodiments described herein. For example, ANOVA, Monte Carlo, etc., and other programs may be implemented.

In one embodiment, a signal can be an external signal 188. Examples of such signals include, but are not limited to, analog signals, digital signals, acoustic signals, optical signals, radio signals, wireless signals, hardwired signals, infrared signals, ultrasonic signals, and the like. In one embodiment, one or more signals may not be encrypted. In one embodiment, one or more signals may be encrypted. In one embodiment, one or more signals may be sent through use of a secure mode of transmission. In one embodiment, one or more signals may be coded for receipt by a specific subject. In one embodiment, such code may include anonymous code that is specific for a subject. Accordingly, information included within one or more signals may be protected against being accessed by others who are not the intended recipient.

Figure 2:
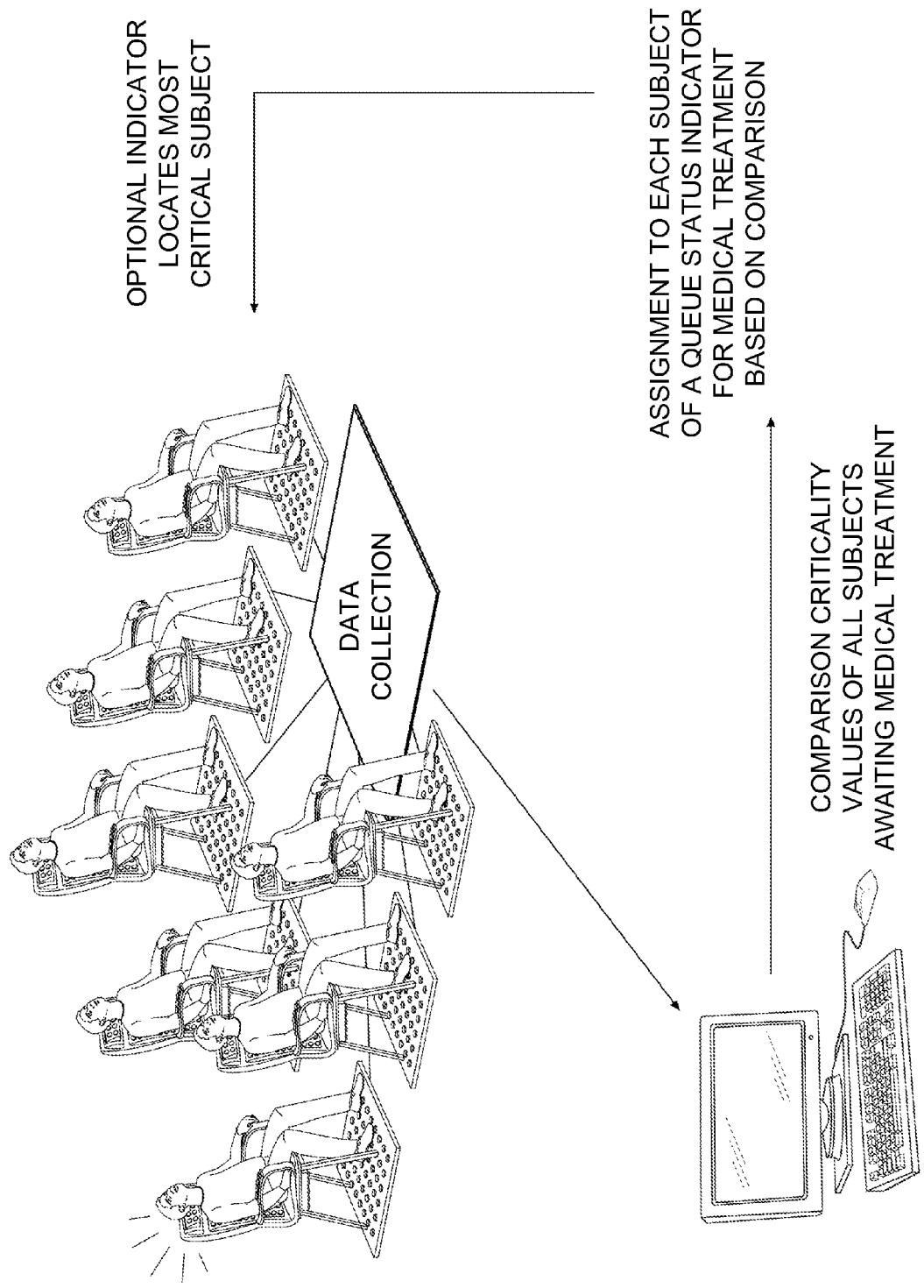
FIG. 2 illustrates a partial view of a particular embodiment described herein.

As shown in FIG. 2, in one embodiment describing methods, systems, and computer program products described herein, one or more subjects are assessed in a healthcare facility, depending on each subject's health condition. The data from each of the subjects is collected and compared with all other subjects awaiting medical treatment. Each subject is assigned a Queue Status Indicator based on the Criticality Value of each subject compared with the rest of the subjects awaiting treatment, and in one embodiment, an optional indicator locates the most critical subject waiting treatment.

In one embodiment, at least one dataset described herein includes a dynamic data structure. In one embodiment, at least one dataset described herein includes a static data structure. In one embodiment, a subject is assessed based on queries of a Characteristic Value dataset. In one embodiment, the Characteristic Value query includes at least one of a DCQ, observed or sensed characteristic, or input based on the subject's health history or health records. In one embodiment, the Characteristic Value query includes a survey from an input/output device, for example. In one embodiment, the survey can be in any language, or in pictorial or other form. In one embodiment, the survey includes skip logic, or conditional branching, that allows for the survey to be customized for the subject based on the subject's previous responses. For example, if a subject's first query includes asking whether the subject is male or female, and the subject answers "female," then the survey skip logic rules could be such that it forces the subject to skip questions related to exclusively male symptoms or conditions.

In one embodiment, a particular Characteristic Value is coupled to the Criticality Value more tightly than another particular Characteristic Value. For example, a heavier weight might be given to a tightly coupled Characteristic Value (e.g., heart rate, respiration, etc.). In one embodiment, one or more Characteristic Values are weighted heavier, thus generating a higher Criticality Value when included in the subject's response, and elevating the subject in the queue. For example, a heavier weight can be given to a characteristic that is sensed or present in the subject's health records, and a lesser weight to a self-reported characteristic, particularly when the data collected appears to be contradictory or inconsistent.

Figure 3:
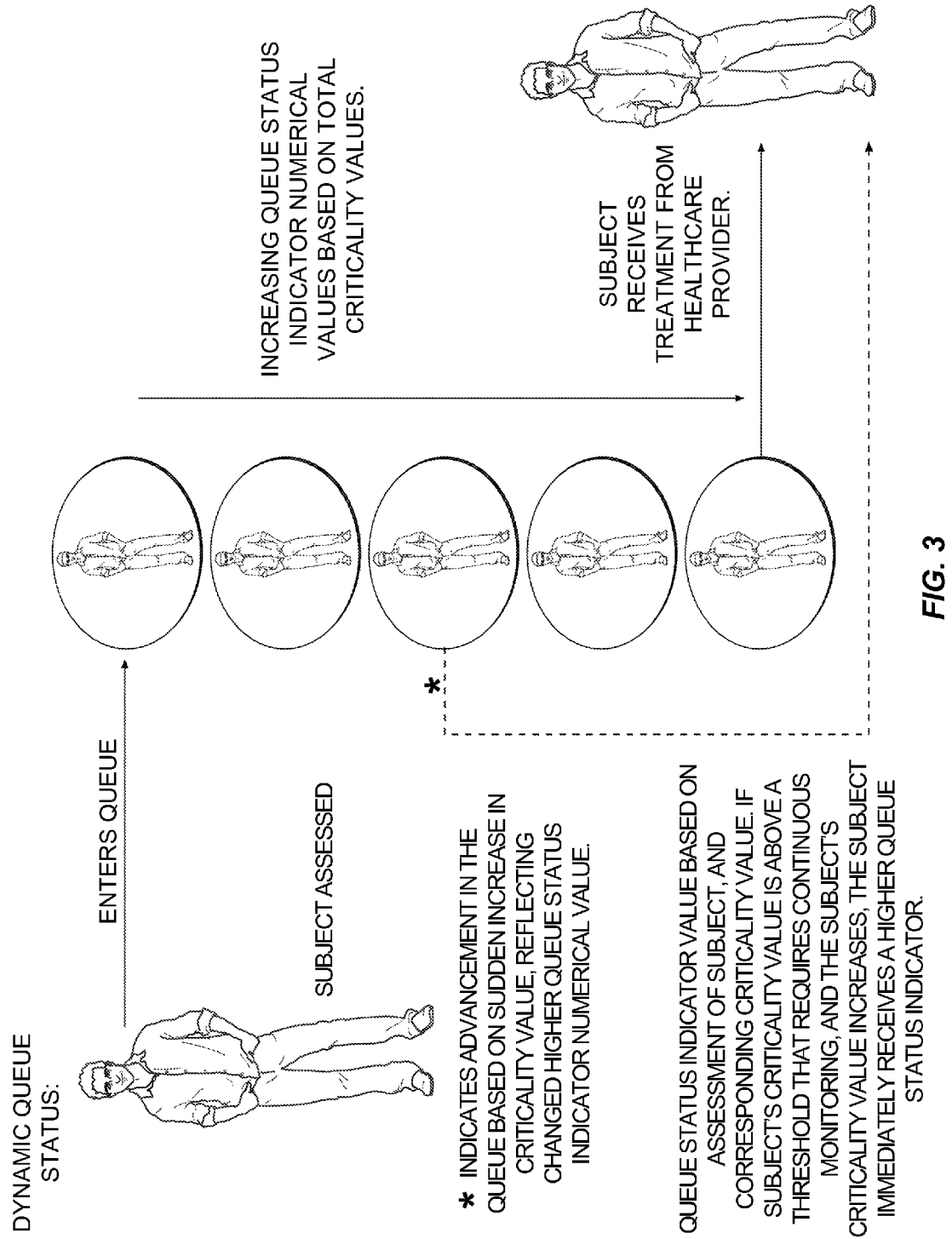
FIG. 3 illustrates a partial view of a particular embodiment described herein.

As shown in FIG. 3, the dynamic dataset described as part of one embodiment of the systems, methods, and computer program products described herein, a first subject is assessed and enters the queue. The Queue Status Indicator of each subject indicates the sequential order in which subjects will receive medical attention. As described, the Queue Status Indicator numerical value is based on the Criticality Value dataset, which in turn is based on the assessment of one or more characteristics of each subject. In one embodiment, if a subject's Criticality Value is above a threshold that requires continuous or intermittent monitoring, and the subject's Criticality Value increases, the QSI dataset is updated, and the subject immediately receives a higher Queue Status Indicator.

As indicated by the asterisk (*) in FIG. 3, a subject who has a sudden increase in Criticality Value has a corresponding increase in his or her Queue Status Indicator and advances in the queue. In the case where the subject's Queue Status Indicator changes dramatically, the subject may be eligible for immediate treatment or next in line medical treatment.

In one embodiment, when a subject has been assessed and assigned a QSI, and the subject's Criticality Value decreases, the updated Criticality Value dataset and updated QSI dataset re-assign a QSI based on the decreased Criticality Value, which may place the subject in a lower or later sequential order compared with the other subjects in the queue. Likewise, when a subject receives medical attention, his or her Criticality Value(s) and QSI are removed from the respective datasets, updating optionally in real time.

Figure 4:
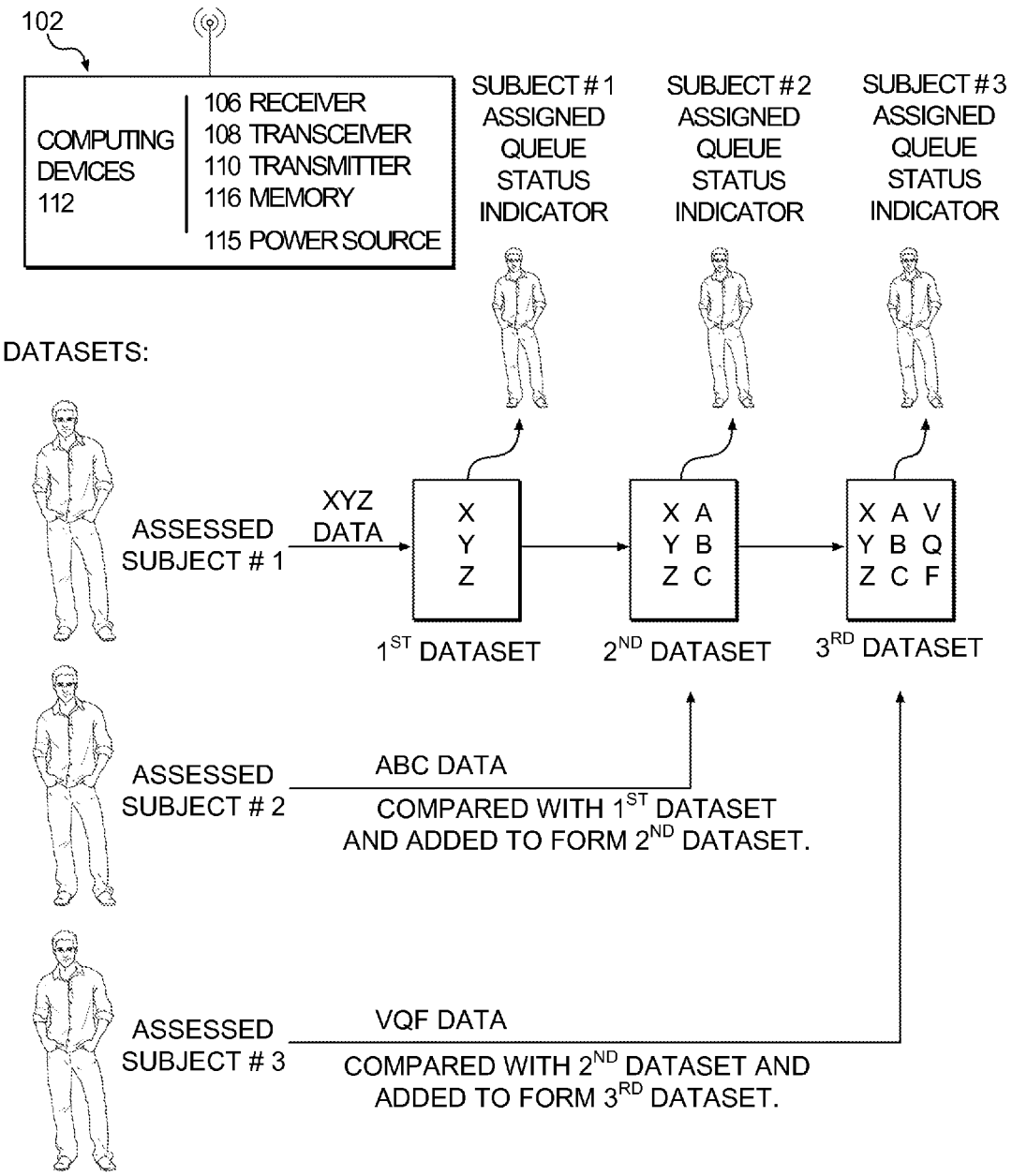
FIG. 4 illustrates a partial view of a particular embodiment described herein.

As shown in FIG. 4, the system 102 includes a computing device 112 with optionally one or more of a receiver 106, transceiver 108, transmitter 110, memory 116, or power source 115. In one embodiment, as described, the dynamic dataset includes a compilation of data from each assessed subject in the queue. For example, Subject #1 is assessed, generating XYZ data (one or more Characteristic Values based on one or more assessed characteristics of the subject), which provide the basis for generation of a Criticality Value for Subject #1 based on the Criticality Value dataset, the XYZ data enters the Criticality Value dataset. Since the Criticality Value dataset was previously empty (or had zero value), the subject is assigned a Queue Status Indicator (in this case #1) accordingly.

Next, Subject #2 is assessed, generating ABC data (one or more Characteristic Values based on one or more assessed characteristics of the subject), which provides the basis for generation of a Criticality Value for the subject based on comparison with the Criticality Value dataset, as ABC data enters the Criticality Value dataset. The data from Subject #2 is compared with the other data in the Criticality Value dataset and the subject is assigned a Queue Status Indicator accordingly.

Finally, Subject #3 is assessed, generating VQF data (one or more Characteristic Values based on one or more assessed characteristics of the subject), which provides the basis for generation of a Criticality Value for the subject based on comparison with the Criticality Value dataset, as VQF data enters the Criticality Value dataset. The data from Subject #3 is compared with the other data in the Criticality Value dataset and the subject is assigned a Queue Status Indicator according to where the subject's Criticality Value ranks with the other subjects' Criticality Values in the dataset.

Addition to the dataset of any number of data from assessed subjects in the queue can cause a shift in the previously assigned Queue Status Indicator of any subject, depending on the Queue Status Indicator assigned to the added subject(s). Likewise, at the time a subject receives medical attention, his or her QSI and Criticality Value data are removed from the respective datasets. Such removal of data can result in a shift in the remaining subjects' Criticality Value(s) and QSI, in response to the dynamic dataset changes.

Figure 5:
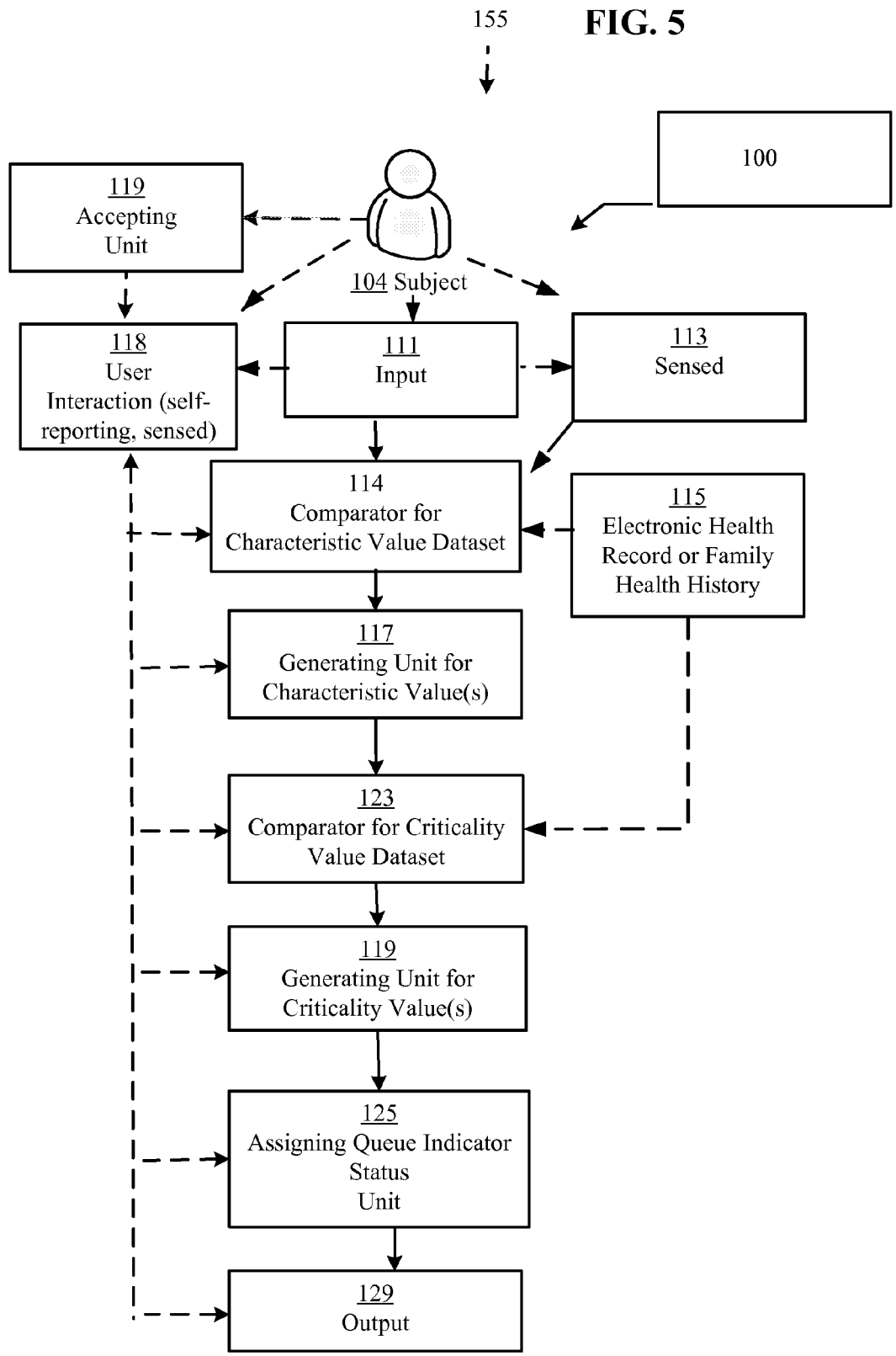
FIG. 5 illustrates a partial view of a particular embodiment described herein.

FIG. 5 illustrates one embodiment that includes a system 155 including at least one computing device 100. The computing device can take various forms or be part of an object, such as a limited resource computing device, a wireless communication device, a mobile wireless communication device, an electronic pen, a handheld electronic writing device, a digital camera, a scanner, an ultrasound device, an x-ray machine, a non-invasive imaging device, a cell phone, a PDA, an electronic tablet device, a medical apparatus (implantable or otherwise), a printer, a car, and an airplane.

The computing device 100 is operably connected to at least one input/output device (see other Figures) for which the subject 104 can interact. For example, in an embodiment, the system 155 includes an accepting unit 119, which interacts with a user 118 (can be self-reported information, sensed information, or information obtained from health history records or family members, etc. given to a health care worker) that causes the input 111. In addition, if one or more sensors are employed, information is sensed 113. The system 155 further includes a comparator for the Characteristic Value dataset 114, which is operably coupled to electronic health records or family health history 115. In an embodiment, the system 155 further includes at least one Generating Unit 117 for one or more Characteristic Values for the subject. In an embodiment, the system 155 includes a Comparator 123 for the Criticality Value Dataset and a Generating Unit for Criticality Value(s) 119. In an embodiment, the system 155 includes an Assigning Queue Indicator Status Unit 125, and output 129.

Figure 6:
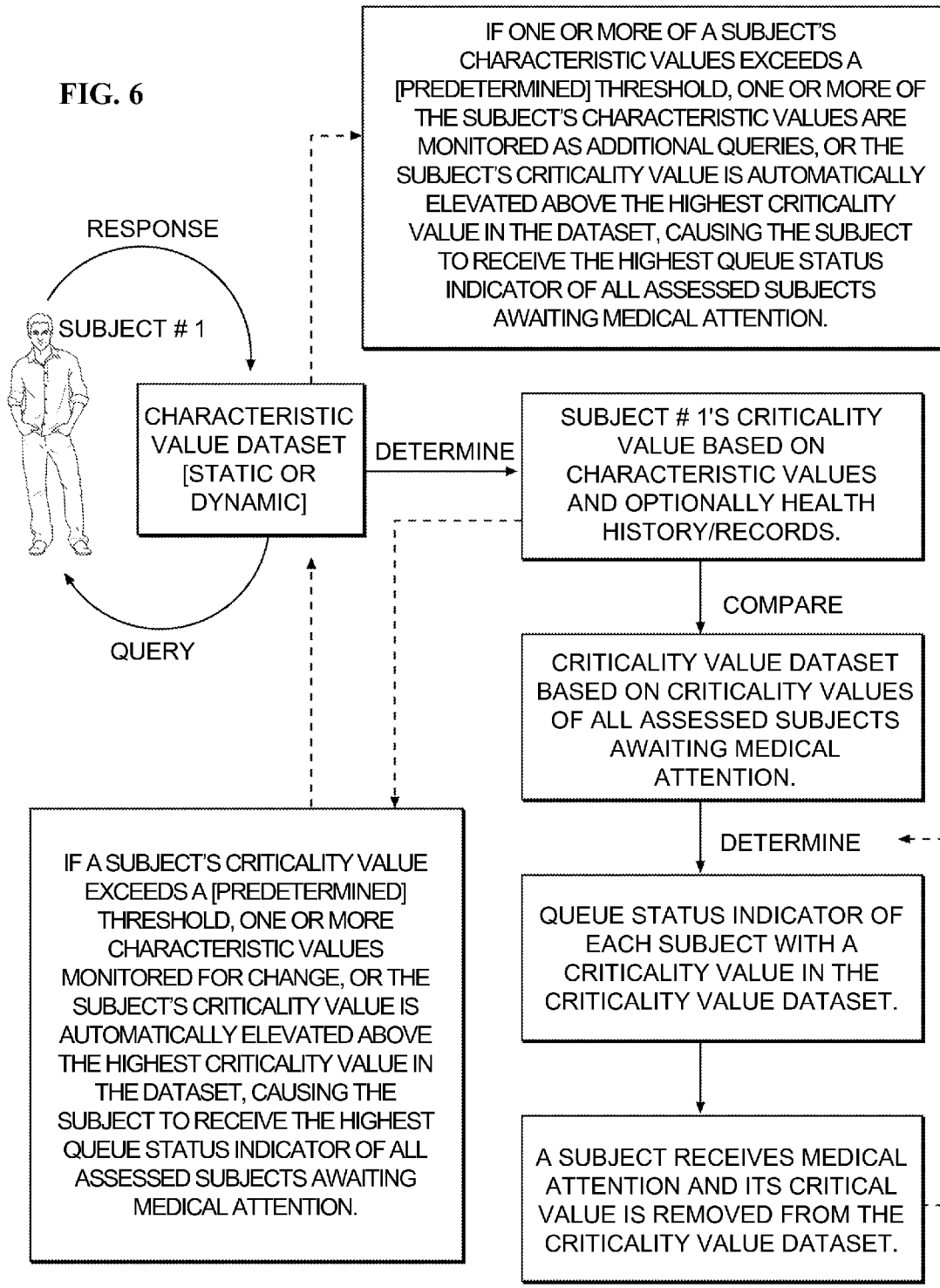
FIG. 6 illustrates a partial view of a particular embodiment described herein.

FIG. 6 indicates an embodiment in which Subject #1 provides a response that generates a Characteristic Value dataset (can be static or dynamic), based on one or more queries, for example. From the Characteristic Value dataset, the Subject #1's Criticality Value Based on Characteristic Values and optionally health history/records are determined. As shown, if one or more of a subject's Characteristic Values exceeds a [predetermined] threshold, one or more of the subject's Characteristic Values are monitored as additional queries, or the subject's Criticality Value is automatically elevated above the highest Criticality Value in the dataset, causing the subject to receive the highest Queue Status Indicator of all assessed subjects awaiting medical attention.

Next, if a subject's Criticality Value exceeds a [predetermined] threshold, one or more Characteristic Values monitored for change, or the subject's Criticality Value is automatically elevated above the highest Criticality Value in the dataset, causing the subject to receive the highest queue status indicator of all assessed subjects awaiting medical attention. In an embodiment, once the subject's Criticality Value has been determined, the Criticality Value is compared with the Criticality Value dataset based on Criticality Values of all assessed subjects awaiting medical attention. Next, the Queue Status Indicator of each subject with a Criticality Value in the Criticality Value dataset is determined. Then a subject receives medical attention and its Critical Value is removed from the Criticality Value dataset.

Figure 7:
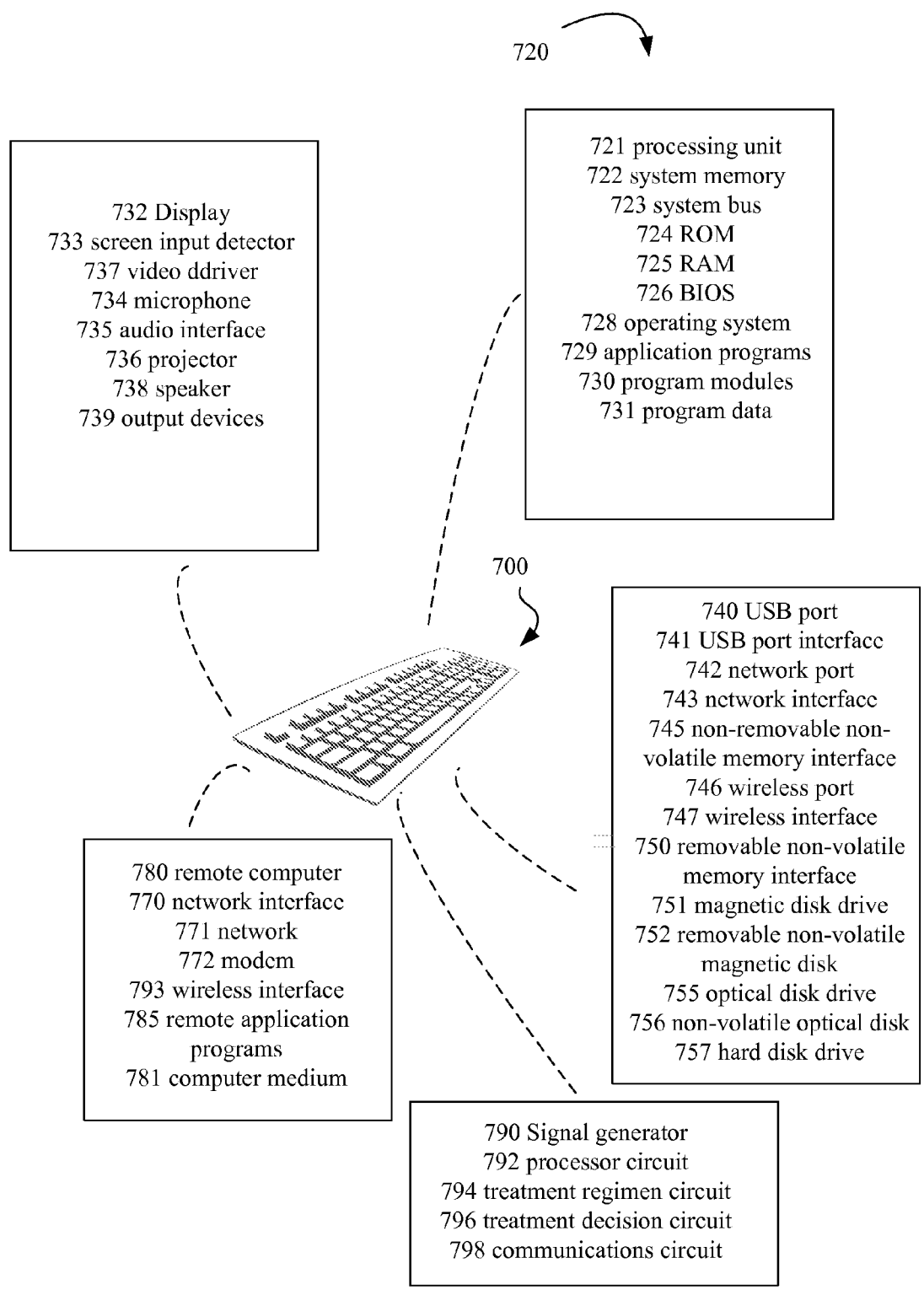
FIG. 7 illustrates a partial view of a particular embodiment described herein.

FIG. 7 illustrates an input/output device 700 operably coupled with a computing device 720 that includes a processing unit 721, a system memory 722, and a system bus 723 that couples various system components including the system memory 722 to the processing unit 721. The system bus 723 may be any of several types of bus structures including a memory bus or memory controller, a peripheral bus, and a local bus using any of a variety of bus architectures. The system bus 723 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus. The system memory includes read-only memory (ROM) 724 and random access memory (RAM) 725. A basic input/output system (BIOS) 726, containing the basic routines that help to transfer information between sub-components within the thin computing device 720, such as during start-up, is stored in the ROM 724. A number of program modules may be stored in the ROM 724 or RAM 725, including an operating system 728, one or more application programs 729, other program modules 730 and program data 731.

A user may enter commands and information into the computing device 720 through input devices, such as a number of switches and buttons, illustrated as hardware buttons 744, connected to the system via a suitable interface 745. Input devices may further include a touch-sensitive display with suitable input detection circuitry, illustrated as a display 732 and screen input detector 733. The output circuitry of the touch-sensitive display 732 is connected to the system bus 723 via a video driver 737. Other input devices may include a microphone 734 connected through a suitable audio interface 735, and a physical hardware keyboard (not shown). Output devices may include at least one the display 732, or a projector display 736.

In addition to the display 732, the computing device 720 may include other peripheral output devices, such as at least one speaker 738. Other external input or output devices 739, such as a joystick, game pad, satellite dish, scanner or the like may be connected to the processing unit 721 through a USB port 740 and USB port interface 741, to the system bus 723. Alternatively, the other external input and output devices 739 may be connected by other interfaces, such as a parallel port, game port or other port. The computing device 720 may further include or be capable of connecting to a flash card memory (not shown) through an appropriate connection port (not shown). The computing device 720 may further include or be capable of connecting with a network through a network port 742 and network interface 743, and through wireless port 746 and corresponding wireless interface 747 may be provided to facilitate communication with other peripheral devices, including other computers, printers, and so on (not shown). It will be appreciated that the various components and connections shown are examples and other components and means of establishing communication links may be used.

The computing device 720 may be designed to include a user interface. The user interface may include a character, a key-based, or another user data input via the touch sensitive display 732. The user interface may include using a stylus (not shown). Moreover, the user interface is not limited to an actual touch-sensitive panel arranged for directly receiving input, but may alternatively or in addition respond to another input device such as the microphone 734. For example, spoken words may be received at the microphone 734 and recognized. Alternatively, the computing device 720 may be designed to include a user interface having a physical keyboard (not shown).

In certain instances, one or more components of the computing device 720 may be deemed not necessary and omitted. In other instances, one or more other components may be deemed necessary and added to the computing device.

In certain instances, the computing system typically includes a variety of computer-readable media products. Computer-readable media may include any media that can be accessed by the computing device 720 and include both volatile and nonvolatile media, removable and non-removable media. By way of example, and not of limitation, computer-readable media may include computer storage media. By way of further example, and not of limitation, computer-readable media may include a communication media.

Computer storage media includes volatile and nonvolatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 720. In a further embodiment, a computer storage media may include a group of computer storage media devices. In another embodiment, a computer storage media may include an information store. In another embodiment, an information store may include a quantum memory, a photonic quantum memory, or atomic quantum memory. Combinations of any of the above may also be included within the scope of computer-readable media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, RF, optical, and infrared media.

The computing device 720 may also include other removable/non-removable, volatile/nonvolatile computer storage media products. For example, such media includes a non-removable non-volatile memory interface (hard disk interface) 745 reads from and writes for example to non-removable, non-volatile magnetic media, or a removable non-volatile memory interface 750 that, for example, is coupled to a magnetic disk drive 751 that reads from and writes to a removable, non-volatile magnetic disk 752, or is coupled to an optical disk drive 755 that reads from and writes to a removable, non-volatile optical disk 756, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 757 is typically connected to the system bus 723 through a non-removable memory interface, such as the interface 745, and magnetic disk drive 751 and optical disk drive 755 are typically connected to the system bus 723 by a removable non-volatile memory interface, such as interface 750.

The drives and their associated computer storage media discussed above provide storage of computer-readable instructions, data structures, program modules, and other data for the computing device 720.

A user may enter commands and information into the computing device 720 through input devices such as a microphone, keyboard, or pointing device, commonly referred to as a mouse, trackball, or touch pad. Other input devices (not shown) may include at least one of a touch sensitive display, joystick, game pad, satellite dish, and scanner. These and other input devices are often connected to the processing unit through a user input interface that is coupled to the system bus, but may be connected by other interface and bus structures, such as a parallel port, game port, or a universal serial bus (USB).

The computing system may operate in a networked environment using logical connections to one or more remote computers, such as a remote computer 780. The remote computer 780 may be a personal computer, a server, a router, a network PC, a peer device, or other common network node, and typically includes many or all of the elements described above relative to the computing device 720, although only a memory storage device. The network logical connections include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing system is connected to the network 771 through a network interface, such as the network interface 770, the modem 772, or the wireless interface 793. The network may include a LAN network environment, or a WAN network environment, such as the Internet. In a networked environment, program modules depicted relative to the computing device 720, or portions thereof, may be stored in a remote memory storage device. By way of example, and not limitation, remote application programs 785 as residing on computer medium 781. It will be appreciated that the network connections shown are examples and other means of establishing communication link between the computers may be used.

In certain instances, one or more elements of the computing device 720 may be deemed not necessary and omitted. In other instances, one or more other components may be deemed necessary and added to the computing device 720.

The signal generator 790 includes a signal generator configured to generate a signal indicative of the sensed characteristic of the subject. In one embodiment, the signal may include a raw data signal, i.e., a capacitance measurement, a change in position of skin over artery in the neck, an acoustic pressure, or a brain electrical activity of the subject. In one embodiment, the signal generator may include a processor circuit 792, a treatment regimen circuit 794, a treatment decision circuit 796, or a communications circuit 798. In one embodiment, the communications circuit may be operable to communicate using an electrical conductor or using a wireless transmission. In one embodiment, the signal generator may include an instance of the thin computing device 720 and the processor circuit may be the processing unit 721.

In one embodiment, the system actively monitors (e.g., detects, tracks, etc.) a subject 104 located by using at least one of computerized axial tomography, fiber optic thermometry, infrared thermography, magnetic resonance imaging, magnetic resonance spectroscopy, microwave thermography, microwave dielectric spectroscopy, positron emission tomography, ultrasound reflectometry, spectroscopic imaging, visual imaging, infrared imaging, single photon emission computed tomography, or the like.

In one embodiment, the system includes a subject tracking system (not shown in figures). For example, in one embodiment, the system includes a subject tracking system for updating in real time a subject's virtual location in a virtual space corresponding to the physical location of the subject in a physical space, such as a healthcare facility or waiting room. In one embodiment, the subject tracking system includes an optical recognition distributed sensor network that generates Criticality Value based in part on the continuous monitoring of the overall physical condition of the subject, including subject's movements, gait, etc.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith. Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, subjectively and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, subjectively and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, subjectively and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Those skilled in the art will appreciate that a user may be representative of a human user, a robotic user (e.g., computational entity), and/or substantially any combination thereof (e.g., a user may be assisted by one or more robotic agents) unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Various non-limiting embodiments are described herein as Prophetic Examples.

PROPHETIC EXAMPLE 1

Automatic Patient Data Collection System for Emergency Department Waiting Room

An automatic data collection system is constructed in an emergency department waiting room and used to prioritize the patients for receiving medical attention by ranking each subject with a Queue Status Indicator (QSI). A prospective patient is registered upon entering the waiting room by interaction with a touch screen computer (e.g., iPad2 from Apple, Inc., Cupertino, Calif.) and a fingerprint sensor (e.g., Lumidigm Venus fingerprint sensor from Lumidigm Inc., Albuquerque, N. Mex.; see Lumidigm Venus Datasheet which is incorporated herein by reference). The computer is programmed to interact verbally and by touch with the patient. The patient is prompted to touch the fingerprint sensor and the fingerprint data is compared to a database (which may be site wide [health care center, hospital, etc.], citywide, statewide or nationwide) of patient medical records. If no matching medical record is found, the computer queries the patient by voice and "on-the-screen" to obtain registration information and to create a new medical record for the patient that includes the fingerprint data. Any verbal information provided by the patient is displayed on the computer screen and confirmed by touching the screen. The touch screen computer also has a camera to record the height of the patient and a facial photograph, which are also transmitted to a central computer and recorded in the medical record. If the patient has a pre-existing medical record, the patient may be queried by the computer to update the medical record. For example, the patient's current address, phone number and insurance coverage may be verified. The computer also asks the patient to choose between automated physiologic data collection and non-automated data collection. If the patient chooses automated data collection then a designated chair in the waiting room is activated, and the patient is directed to sit in the chair designated by a flashing light.

The designated chair in the waiting room contains interacting sensors to verify the patient's identity and to measure and record physiological parameters of the patient. When the patient sits down, the patient is prompted by a flashing light to touch a fingerprint sensor on the chair (sensor may be directly touching the subject). Once the patient touches the screen or otherwise engages the system, the available space flashing light indicator stops. Recognition of the patient's fingerprint by a central computer results in successive activation of sensors to determine the patient's weight, electrocardiogram, heart rate, respiration rate, temperature, and blood oxygen level. The patient's weight is determined by an electronic scale under the chair, which automatically transmits the weight and date to a central computer containing the patient's medical record(s). The patient's electrocardiogram is determined by electric potential sensors, which may be placed 1 meter apart on opposite sides of the chair (not directly touching the subject). Nonconductive electric potential sensors to determine a patient's electrocardiogram are described (see e.g., Harland et al., *Meas. Sci. Technol.* 13, 163-169, 2002, which is incorporated herein by reference). The patient's respiration rate and heart rate may be determined by a remote sensor that detects physiological activities by illuminating the patient with radio frequency (RF) electromagnetic signals and detecting the reflected electromagnetic signal waves. The sensor may be incorporated in the back of the chair. A remote sensor to detect respiration and heart rate is described (see e.g., U.S. Pat. No. 7,272,431, which is incorporated herein by reference). The patient's body temperature is determined by thermal imaging with a radiometric camera (e.g., a 7320 ETIP camera available from Infrared Cameras, Inc., Beaumont, Tex.; see Spec. Sheet IR camera, which is incorporated herein by reference). The infrared camera is installed in the wall in front of the patient's chair and focused on the patient's forehead or eyes. Devices and methods to determine core body temperature noninvasively and remotely are described (see e.g., U.S. Pat. No. 7,340,293, which is incorporated herein by reference).

The patient's hematocrit and blood oxygen concentration are determined by a photoplethysmograph device on the armrest of the chair. A system with a finger clip emits and detects different wavelengths of light through the tissue of the finger (see e.g., Shaltis, et al., *Conf. Proc. IEEE Eng. Med. Biol. Soc.* 4: 3567-3570, 2005, which is incorporated herein by reference). The extinction of selected wavelengths of light is detected and may be used to determine the hematocrit and the blood oxygen saturation value. For example, a system and method to measure hematocrit and blood oxygenation by transilluminating the patient's finger with light at wavelengths of 660 nm, 805 nm and 1550 nm is described (see e.g., U.S. Pat. No. 5,372,136, which is incorporated herein by reference). The biometric and physiological parameters determined remotely by the automatic data collection system in the waiting room are transmitted wirelessly to a central computer that communicates with health information databases (e.g., Kaiser Permanente electronic health records may be accessed using EpicCare software from Epic Systems Corp, Verona, Wis.; and Centers for Disease Control, Data and Statistics are available online at: cdc.gov/datastatistics, the subject matter of which is incorporated herein by reference). Wireless sensor networks for aggregating and transmitting physiological data to a central computer are described (see e.g., Gao et al., *Proc. IEEE Conf. Technologies for Homeland Security*, pp. 187-192, 2008, which is included herein by reference).

The automatic data collection system includes computer programs and methods to compare the patient's physiological parameters to parameters obtained, for example, from healthy individuals, to the patient's medical history, and most importantly, to the dataset obtained from each prospective patient that enters the emergency department waiting room. The system includes a central computer with programs to compare datasets from the emergency room patients and prioritize the patients for medical attention. Computer programs to evaluate and compare physiological datasets are described (see e.g., the paper titled: *OSCAR-MDA An Artificially Intelligent Advisor for Emergency Room Medicine* by John L. Pollock and Devin Hosea printed on Oct. 18, 2011 and available online at citeseerx.ist.psu.edu/viewdoc/download?doi=10.1.1.49.4970&rep=rep&type=pdf and Pollock, *Cognitive Carpentry: A Blueprint for How to Build a Person*, MIT Press, Cambridge, Mass., 1995, each of which is incorporated herein by reference.) Once a patient is assessed, and his or her Characteristic Value(s) are generated based on the assessed characteristics, a Criticality Value is generated by comparison with the Criticality Values of the other patients already in the queue. From this comparison, a Queue Status Indicator is assigned to the patient, ranking him among others in the queue awaiting medical attention. A list of the prioritized patients, their location (e.g., designated waiting room chair), and their biometric and physiological data are transmitted to triage nurses in the Emergency Room who attend to the patients in the order indicated by the Queue Status Indicator.

The identity of the patients is verified by repeating the fingerprint scan using the fingerprint sensor and comparing the fingerprint data to a database containing electronic medical records. The designated chair occupied by the patient is converted to unoccupied status once the triage nurse verifies the patient's identity and attends to the patient.

PROPHETIC EXAMPLE 2

Automatic Patient Data Collection System for Hospital Healthcare Workers

A nurse who cares for patients receiving hematopoietic stem cell transplants is screened by an automatic data collection system for evidence of infectious disease or the presence of a pathogen before gaining access to the hospital. Such a determination can be based at least in part, on the subject's own health history or on standardized values. A hospital pre-entry room contains remote sensors which are wirelessly connected to a central computer that is programmed to compile and analyze the biometric and physiological data obtained from the nurse. The nurse is identified by iris scanning with a wall-mounted iris scanner (e.g., an Iris Scanner System is available from Bayometric, Inc., San Jose, Calif.; see Biometric Iris Access Specif. Sheet which is incorporated herein by reference). The iris scanner system transmits iris images and face images to a central computer that compares the images to stored data to authenticate the nurse's identity. After authentication, the central computer activates a video camera and remote sensors to detect signs of infectious disease in the nurse.

A video is recorded while the nurse is screened by remote sensors. First, an electronic nose is activated to sample the employee's breath and detect chemicals indicative of microbial infection. For example, an electronic sensor array may detect gases indicative of a respiratory infection by pathogens, such as influenza virus, rhinovirus, adenovirus, *Streptococcus, Staphylococcus,* and *Mycobacterium tuberculosis*. Methods and devices to detect chemicals given off by microbial pathogens are described (see e.g., U.S. Patent Application No. 2004/0006257, which is incorporated herein by reference). Electronic nose sensor array response profiles may be used to distinguish healthy and diseased individuals or carriers and non-carriers of a pathogen. Also a database of response profiles corresponding to healthy and infected individuals or carriers and non-carriers of a pathogen may be stored on the central computer and used for comparison to the nurse's current response profile. Stored electronic nose response profiles may include profiles unique to many different bacterial, viral and fungal pathogens. Results from the electronic nose screening are compiled in the central computer for analysis and a remote sensor is activated to measure body temperature. The nurse's body temperature is determined by thermal imaging with a radiometric camera (e.g., a 7320 ETIP camera available from Infrared Cameras, Inc., Beaumont, Tex.; see Spec. Sheet IR Camera, which is incorporated herein by reference). The infrared camera is installed in the wall in the pre-entry room and is focused on the nurse's forehead or eyes. Devices and methods to determine core body temperature noninvasively and remotely are described (see e.g., U.S. Pat. No. 7,340,293, which is incorporated herein by reference). The body temperature is wirelessly transmitted to a central computer and compared to the nurse's mean body temperature for the previous month. Moreover the nurse's physiologic data including the electronic nose response profile, the body temperature and the video data are analyzed by the central computer using dedicated software to determine if the nurse displays signs of infection. Computer programs to evaluate and compare physiological datasets are described (see e.g., the paper titled: *OSCAR-MDA An Artificially Intelligent Advisor for Emergency Room Medicine* by John L. Pollock and Devin Hosea printed on Oct. 18, 2011 and available online at citeseerx.ist.psu.edu/viewdoc/download?doi=10.1.1.49.4970&rep=rep1&type=pdf and Pollock, *Cognitive Carpentry: A Blueprint for How to Build a Person*, MIT Press, Cambridge, Mass., 1995, which are incorporated herein by reference).

If video analysis or any other sensors (i.e., electronic nose and IR camera) indicate an infection may be present, the nurse may be denied access to the hospital until he or she talks with their immediate supervisor or a health safety officer for clearance. If an infection is suspected, the nurse may be required to submit an oral or nasal sample for analysis of microbial pathogens. The sample may be analyzed on a microfluidic chip located in the pre-entry room that utilizes biochemical assays for nucleic acids derived from microbial pathogens. For example, a microfluidic chip designed to detect viral and bacterial pathogens using polymerase chain reaction is described (see e.g., Chen et al, *Ann. N.Y. Acad. Sci.* 1098: 429-436, 2007, which is incorporated herein by reference). Data on detection of viral or bacterial pathogens (e.g., influenza virus, rhinovirus, adenovirus, *Streptococcus pneumoniae, Staphylococcus aureus,* and/or *Mycobacterium tuberculosis*) are automatically transmitted to a central computer by the system, and the nurse, the supervisor, or a health safety officer is notified. If a pathogenic infection is detected, the nurse will be sent home for the day or heightened precautions may be taken, such as the nurse wearing a face mask and avoiding unnecessary contact with patients.

PROPHETIC EXAMPLE 3

Automatic Patient Data Collection System for the Waiting Room of a Primary Care Clinic An adult patient makes an appointment to see a primary care physician due to chest pressure. The patient interacts with an automatic data collection system upon arrival at the doctor's office. The automatic data collection system includes a touch screen computer with a video camera; remote, nonconductive physiological sensors; a central computer and programming to collect and compare a patient's physiological data to electronic health records; and health information database(s).

Upon entering the waiting room, the patient can check in with a receptionist or with a touch screen computer installed adjacent to the reception desk. The patient is registered by interaction with a touch screen computer (e.g., iPad2 from Apple, Inc., Cupertino, Calif.) and a fingerprint sensor (e.g., Lumidigm Venus fingerprint sensor from Lumidigm Inc., Albuquerque, N. Mex.; see Lumidigm Venus Datasheet which is incorporated herein by reference). The touch screen computer is programmed to interact verbally and by touch with the patient, so that any verbal information provided by the patient is displayed on the computer screen and confirmed by touching the screen. The patient is prompted to touch the fingerprint sensor, and the patient's name and fingerprint data are transmitted to a central computer, and compared to a database (which may be site wide, citywide, statewide or nationwide) of patient medical records. If no matching medical record is found, the touch screen computer queries the patient by voice and "on-the-screen" to obtain essential information including name, address, birth date, health insurance information, credit card number, and the reason for the visit. The patient information is sent to the central computer and added to an existing health record, or is used to create a new medical record for the patient that includes the fingerprint data. The touch screen computer also has a camera to record the height of the patient and a facial photograph, which are also transmitted to the central computer and recorded in the medical record(s). If the patient has a pre-existing medical record the patient may be queried by the touch screen computer to update the medical record. For example, the patient's current address, phone number, and insurance coverage may be verified by interacting verbally or by touching the computer keyboard or screen.

The patient is asked to choose between automatic physiologic data collection by remote, nonconductive sensors, or by manual data collection by a healthcare worker at the time of the appointment. If the patient chooses automated data collection, then a designated chair in the waiting room is activated, and the patient is directed to sit in the chair designated by a flashing light. When the patient sits in the designated chair, the flashing light stops, and an electronic scale in the floor measures the patient's weight and sends it to the central computer, which calculates the body mass index (BMI) of the patient and finds the patient is overweight with a BMI equal to 35. Based on the patient's weight and complaint of chest pressure, the system activates remote sensors to measure heart function.

First, a remote, nonconductive sensor is activated to measure the patient's respiration rate and heart rate. A remote sensor illuminates the patient with radio frequency (RF) electromagnetic signals and detects the reflected electromagnetic signal waves. The RF sensor may be incorporated in the back of the chair. A remote sensor to detect respiration and heart rate is described (see e.g., U.S. Pat. No. 7,272,431, which is incorporated herein by reference). Data on the heart rate and respiration rate of the patient are transmitted to a central computer and compared to the patient's previous data on heart rate and respiration rate, as well as normal healthy values for these physiological parameters. The computer determines that the patient's heart rate is abnormal and sends an email message to the physician indicating an abnormal heartbeat is occurring. The central computer also activates a remote nonconductive sensor to determine the patient's electrocardiogram. Ultra-high-input-impedance electric potential sensors in each armrest of the chair adjacent to the patient's arms or torso obtain a single, or together a differential, measurement of the electrical potential signals of the heart. Nonconductive electric potential sensors to determine a patient's electrocardiogram (ECG) are described (see e.g., Harland et al., *Meas. Sci. Technol.* 13, 163-169, 2002, which is incorporated herein by reference). For example, a first order, differential, high resolution ECG is recorded using two electric potential probes, and is transmitted to a central computer where it is compared to previous ECGs for the patient and to ECGs from normal, healthy individuals. The shape and time intervals for the P wave, QRS complex and T wave are evaluated. Computer analysis of the patient's electrocardiogram verifies the abnormal heartbeat detected with the RF sensor and sends another email to the physician highlighting the abnormal ECG aspects and recommending additional evaluation of heart function, such as a 12-electrode ECG and blood biochemistry assays that may provide indications of heart dysfunction. For example, the computer may recommend determining blood electrolytes (e.g., sodium and potassium), measures of renal function, measures of liver function, a complete blood count and measures of blood concentrations of troponin and B-type natriuretic peptide.

Next, the patient's hematocrit and blood oxygen concentration is determined by a photoplethysmograph device on the armrest of the chair. A system with a finger clip emits and detects different wavelengths of light through the tissue of the finger (see e.g., Shaltis, et al., *Conf. Proc. IEEE Eng. Med. Biol. Soc.* 4: 3567-3570, 2005, which is incorporated herein by reference). The extinction of selected wavelengths of light is detected and may be used to determine the hematocrit and the blood oxygen saturation value. For example, a system and method to measure hematocrit and blood oxygenation by transilluminating the patient's finger with light at wavelengths of 660 nm, 805 nm and 1550 nm is described (see e.g., U.S. Pat. No. 5,372,136, which is incorporated herein by reference).

The central computer next activates an infrared camera to measure the patient's temperature. The patient's body temperature is determined by thermal imaging with a radiometric camera (e.g., a 7320 ETIP camera available from Infrared Cameras, Inc., Beaumont, Tex.; see Spec. Sheet IR camera which is incorporated herein by reference). The infrared camera is installed in the wall in front of the patient's chair and focuses on the patient's forehead or eyes. Devices and methods to determine core body temperature in a noninvasive and remote manner are described (see e.g., U.S. Pat. No. 7,340,293, which is incorporated herein by reference). The patient's temperature is transmitted to the central computer and added to their medical record.

The physiological parameters determined remotely by the automatic data collection system in the waiting room are transmitted wirelessly to a central computer that communicates with health information databases (e.g., Kaiser Permanente electronic health records may be accessed using EpicCare software from Epic Systems Corp, Verona, Wis.; Centers for Disease Control, Data and Statistics are available online at cdc.gov/datastatistics, the subject matter of which is incorporated herein by reference). Wireless sensor networks for aggregating and transmitting physiological data to a central computer are described (see e.g., Gao et al., *Proc. IEEE Conf. Technologies for Homeland Security, pp. 187-192, 2008*, which is incorporated herein by reference).

The automatic data collection system includes computer programs and methods to compare the patient's physiological parameters to parameters obtained from healthy individuals, and to the patient's medical history. The system includes a central computer with programs to compare multiple datasets, identify acute care situations and alert and advise healthcare workers. Computer programs to evaluate and compare physiological datasets are described (see e.g., *OSCAR-MDA An Artificially Intelligent Advisor for Emergency Room Medicine*, OSCAR-DSS, OSCAR Project Technical Report, 1997, by John L. Pollock and Devin Hosea printed on Oct. 18, 2011 and available online at citeseerx.ist.psu.edu/viewdoc/download?doi=10.1.1.49.4970&rep=rep1&type=pdf, and Pollock, *Cognitive Carpentry: A Blueprint for How to Build a Person*, MIT Press, Cambridge, Mass., 1995, which are incorporated herein by reference). An updated medical record including the current physiological parameters is provided to the health care giver (e.g., primary care physician) prior to seeing the patient. Moreover, acute medical situations are indicated by alerts issued by the system, based on the assessed characteristics of the patient in comparison with the Criticality Value dataset.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system in a healthcare facility, comprising:
   one or more input/output devices having a non-transitory signal bearing medium operable to
   receive at least one input regarding one or more characteristics of a subject in the healthcare facility, based on at least one sensor located in furniture or equipment configured to support the subject;
   compare the at least one input regarding the subject with a Characteristic Value dataset;

generate a Characteristic Value from the at least one input regarding the subject based on the comparison with the Characteristic Value dataset;

reinitiate receiving at least one input regarding one or more characteristics of the subject, comparing at least one input with a Characteristic Value dataset, and generating a Characteristic Value from the at least one input regarding the subject based on the comparison with the Characteristic Value dataset until an assessment threshold is satisfied;

generate a Criticality Value for the subject based on a weighted determination of the subject's Characteristic Values;

compare the Criticality Value of the subject with a Criticality Value dataset, the Criticality Value dataset including Criticality Values previously generated for the subject based on his or her own health history and including Criticality Values previously generated for other subjects in the hospital room in a queue;

communicate an output indicative of the Criticality Value of the subject to a user;

generate a Queue Status Indicator from a Queue Status Indicator dataset based on the comparing of the Criticality Value of the subject with the Criticality Value dataset derived from among subjects in the same location;

communicate a locational indicator of the subject with the highest priority for medical treatment based on its assignment with a Queue Status Indicator that exceeds a threshold value, and directing at least one health care worker to provide medical treatment to the subject with the highest priority for medical treatment.

2. The system of claim 1, wherein the assessment threshold includes one or more of time, characteristic value, or sequential number.

3. The system of claim 1, wherein the at least one input regarding the subject includes at least one input in response to one or more queries.

4. The system of claim 3, wherein subsequent one or more queries are based on previous input or response by the subject to a previous query.

5. The system of claim 1, wherein the at least one input regarding the subject includes at least one input from a healthcare worker or device regarding the subject.

6. The system of claim 1, wherein the subject is nonresponsive.

7. The system of claim 1, wherein the at least one input regarding the subject includes at least one result from a physiologic assessment of the subject.

8. The system of claim 7, wherein the physiologic assessment includes at least one of an electronic measurement, biological assay, or biochemical assay.

9. The system of claim 1, wherein the at least one input regarding the subject includes one or more detected physiologic parameters sensed by one or more sensors assessing the subject.

10. The system of claim 1, wherein the comparing at least one input regarding the subject with a Characteristic Value dataset includes at least one of coupling, versioning, or clustering in determining the subject's one or more Characteristic Values.

11. The system of claim 3, wherein the queries are linked to the Characteristic Value dataset.

12. The system of claim 1, wherein the input/output device is operable to convert information into electronic signals that include digitized or weighted protocols.

13. The system of claim 1, wherein the system includes one or more logic devices.

14. A system in a healthcare facility, comprising:

one or more computing devices operable to receive at least one input regarding one or more characteristics of a subject in the healthcare facility, based on at least one sensor located in furniture or equipment configured to support the subject;

compare the at least one input regarding the subject with a Characteristic Value dataset;

generate a Characteristic Value from the at least one input regarding the subject based on the comparison with the Characteristic Value dataset;

reinitiate receiving at least one input regarding one or more characteristics of the subject, comparing at least one input with a Characteristic Value dataset, and determining a Characteristic Value from the at least one input regarding the subject based on the comparison with the Characteristic Value dataset until the comparison satisfies a threshold condition;

generate a Criticality Value for the subject based on a weighted determination of the subject's Characteristic Values;

compare the Criticality Value of the subject with a Criticality Value dataset, the Criticality Value dataset including Criticality Values previously generated for the subject based on his or her own health history and including Criticality Values previously generated for other subjects in the hospital room in a queue;

communicate an output indicative of the Criticality Value of the subject to a user;

generate a Queue Status Indicator from a Queue Status Indicator dataset based on the comparing of the Criticality Value of the subject with the Criticality Value dataset derived from among subjects in the same location;

communicate a locational indicator of the subject with the highest priority for medical treatment based on its assignment with a Queue Status Indicator that exceeds a threshold value, and directing at least one health care worker to provide medical treatment to the subject with the highest priority for medical treatment.

15. A system in a healthcare facility, comprising:

one or more Critical Value generation devices having a non-transitory signal bearing medium operable to receive at least one input regarding one or more characteristics of a subject in the healthcare facility, based on at least one sensor located in furniture or equipment configured to support the subject;

compare the at least one input regarding the subject with a Characteristic Value dataset;

generate a Characteristic Value from the at least one input regarding the subject based on the comparison with the Characteristic Value dataset;

reinitiate receiving at least one input regarding one or more characteristics of the subject, comparing at least one input with a Characteristic Value dataset, and determining a Characteristic Value from the at least one input regarding the subject based on the comparison with the Characteristic Value dataset until the comparison satisfies a threshold condition;

generate a Criticality Value for the subject based on a weighted determination of the subject's Characteristic Values;

compare the Criticality Value of the subject with a Criticality Value dataset, the Criticality Value dataset including Criticality Values previously generated for the subject based on his or her own health history and including Criticality Values previously generated for other subjects in the hospital room in a queue;

communicate an output indicative of the Criticality Value of the subject to a user;

generate a Queue Status Indicator from a Queue Status Indicator dataset based on the comparing of the Criticality Value of the subject with the Criticality Value dataset derived from among subjects in the same location;

communicate a locational indicator of the subject with the highest priority for medical treatment based on its assignment with a Queue Status Indicator that exceeds a threshold value, and directing at least one health care worker to provide medical treatment to the subject with the highest priority for medical treatment.

16. A system in a healthcare facility, including a computer processor, the system comprising:

circuitry configured for receiving at least one input regarding one or more characteristics of a subject in the healthcare facility, based on at least one sensor located in furniture or equipment configured to support the subject;

circuitry configured for comparing at least one input regarding the subject with a Characteristic Value dataset;

circuitry configured for determining a Characteristic Value from the at least one input regarding the subject based on the comparison with the Characteristic Value dataset;

circuitry configured for repeating receiving at least one input regarding one or more characteristics of the subject, comparing the at least one input with a Characteristic Value dataset until a comparison with the Characteristic Value dataset satisfies a threshold condition;

circuitry configured for generating a Criticality Value for the subject based on a weighted determination of the subject's Characteristic Values;

circuitry configured for comparing the Criticality Value of the subject with a Criticality Value dataset, the Criticality Value dataset including Criticality Values for the subject based on his or her own health history and including Criticality Values previously generated for other subjects in the hospital room in a queue;

circuitry configured for communicating an output indicative of the Criticality Value of the subject to a user;

circuitry for generating a Queue Status Indicator from a Queue Status Indicator dataset based on the comparing of the Criticality Value of the subject with the Criticality Value dataset;

circuitry for communicating a locational indicator of the subject with the highest priority for medical treatment based on its assignment with a Queue Status Indicator that exceeds a threshold value, and circuitry for directing at least one health care worker to provide medical treatment to the subject with the highest priority for medical treatment.

17. The system of claim 16, further including circuitry for storing at least one of the one or more Characteristic Values, the one or more Criticality Value, or the Queue Status Indicator value for the subject.

18. The system of claim 16, further including:

circuitry for recording, responsive to the circuitry for accepting data related to a subject;

responsive to the circuitry for receiving at least one input regarding one or more characteristics of the subject;

responsive to the circuitry for comparing at least one input regarding one or more characteristics of the subject with the Characteristic Value dataset;

responsive to the circuitry for determining a Characteristic Value from the at least one input regarding the subject based on the comparison with the Characteristic Value dataset;

responsive to the circuitry for repeating reinitiating receiving the at least one input regarding one or more characteristics of the subject and comparing the at least one input regarding the subject with the Characteristic Value dataset until a comparison with the Characteristic Value dataset satisfies a threshold condition;

responsive to the circuitry for generating a Criticality Value for the subject based on a weighted determination of the subject's Characteristic Values;

responsive to the circuitry for comparing the Criticality Value of the subject with a Criticality Value dataset, the Criticality Value dataset including Criticality Values previously generated for the subject based on his or her own health history; and responsive to communicating an output indicative of the Criticality Value of the subject to a user.

19. A system in a healthcare facility, including a computer processor, comprising:

circuitry for receiving one or more signals transmitted in response to generating one or more of a subject's Characteristic Values, or a subject's Criticality Value based on receiving at least one input regarding one or more characteristics of the subject in the healthcare facility, based on at least one sensor located in furniture or equipment configured to support the subject;

circuitry for comparing the Criticality Value of the subject with a Criticality Value dataset, the dataset including Criticality Values previously generated for the subject based on his or her own health history and including Criticality Values previously generated for other subjects in the hospital room in a queue;

circuitry for assigning a Queue Status Indicator based on the comparison of the subject's Criticality Value with the Criticality Value dataset derived from among subjects in the same location;

circuitry for indicating location of one or more subjects with the highest priority for medical treatment based on the assigned Queue Status Indicator in response to assessing the subject, and circuitry for directing at least one health care worker to provide medical treatment to the subject with the highest priority for medical treatment.

20. The system of claim 19, further including:

circuitry for recording, responsive to the circuitry for receiving one or more signals transmitted in response to generating one or more of the subject's Characteristic Values, or the subject's Criticality Value;

responsive to the circuitry for comparing the Criticality Value of the subject with a Criticality Value dataset, the dataset including Criticality Values previously generated for the subject based on his or her own health history;

responsive to the circuitry for assigning a Queue Status Indicator based on the comparison of the subject's Criticality Value with the Criticality Value dataset;

responsive to the circuitry for indicating location of one or more subjects with the highest priority for medical treatment based on their assigned Queue Status Indicator in response to the receiving at least one input regarding the subject, on a non-transitory signal bearing medium.

\* \* \* \* \*